United States Patent [19]
Henningsen et al.

[11] Patent Number: 5,946,095
[45] Date of Patent: Aug. 31, 1999

[54] NATURAL GAS DETECTION APPARATUS AND METHOD OPERABLE IN A MOVING VEHICLE

[75] Inventors: Tom Henningsen, Monroeville; Tod A. Oblak, Pittsburgh; Max Garbuny, Butler; John M. Zomp, N. Huntingdon, all of Pa.; L. L. (Tom) Altpeter, Jr., Arlington Heights, Ill.

[73] Assignees: Gas Research Institute, Chicago, Ill.; Westinghouse Electric Corporation, Pittsburgh, Pa.

[21] Appl. No.: 08/812,281

[22] Filed: Mar. 6, 1997

Related U.S. Application Data

[60] Provisional application No. 60/013,079, Mar. 8, 1996.

[51] Int. Cl.$^6$ ........................................ G01B 9/02
[52] U.S. Cl. ............................. 356/346; 356/352
[58] Field of Search ................... 356/346, 352; 250/338.5, 339.07, 339.08

[56] References Cited

U.S. PATENT DOCUMENTS

| 4,195,931 | 4/1980 | Hara | 356/352 |
|---|---|---|---|
| 5,076,699 | 12/1991 | Ryan et al. | 356/346 |

FOREIGN PATENT DOCUMENTS

| 1528123 A1 | 7/1992 | U.S.S.R. | 356/352 |

*Primary Examiner*—Samuel A. Turner
*Attorney, Agent, or Firm*—Pauley Petersen Kinne & Fejer

[57] ABSTRACT

A natural gas detection system is provided for use with a vehicle. A natural gas detector apparatus is mounted to the vehicle so that the vehicle transports the detector apparatus over an are of interest at speeds of up to 20 miles per hour. The detector apparatus includes a transmitter section and a receiver section displaced a preselected distance from each other. The transmitter section has a light source transmitting a light beam to the receiver section forming a beam path therebetween. The apparatus is arranged such that natural gas intercepts the beam path and absorbs representative wavelengths of the light beam. The receiver section receives a portion of the light beam onto an electro-optical etalon for detecting the gas. A method of detecting natural gas is also provided. The method has the steps of providing a vehicle and mounting a natural gas detector apparatus to the vehicle. The detector apparatus has a transmitter section and a receiver section displaced a preselected distance from each other. The transmitter section includes a light source. The method includes transmitting a light beam in a beam path from the transmitter section to the receiver section, and driving the vehicle over an area of interest so that natural gas intercepts the beam path and absorbs representative wavelengths of the light beam. Fhe method also includes receiving a portion of the light beam in the receiver section so that the light beam is directed into an etalon, and detecting a gas leak in the area of interest from the portion light beam using the gas detection apparatus mounted on the vehicle while the vehicle is in motion.

12 Claims, 18 Drawing Sheets

FIG. 12 TRANSMISSION OF REFLECTIVE ETALON

|   | A | B | C | D | E | F | G | H |
|---|---|---|---|---|---|---|---|---|
| 1 | INPUT PARAMETERS: | | | | ETALON CALCULATIONS: | | | |
| 2 | ETALON REFLECTIV(%)= | | 70 | | LENGTH, nl (cm) = | | | 0.049 |
| 3 | FREE SPEC RANGE (cm-1) | | 10.3 | | RESOLUTION (cm-1) = | | | 1.176 |
| 4 | GAS CONC (ppm x cm)= | | 100 | | TOTAL MOLECULES = | | | 2.68E + 15 |
| 5 | FREQUENCY: | | | | | | | |
| 6 | CENTER (cm-1) = | | 2958.2 | | | | | |
| 7 | UPPER LIMIT (cm-1) = | | 2990 | | | | | |
| 8 | LOWER LIMIT (cm-1) = | | 2910 | | | | | |
| 9 | MODULATION(% OF RANGE | | 58.5 | | | | | |
| 10 | TOTAL INTENSITY IN WINDOW(cm-1) = | | | | | | 80.00 | |
| 11 | INTENSITY TRANSMITTED BY ETALON(cm-1) = | | | | | | 14.12 | |
| 12 | RATIO ABSORPTION: (ON LINE)/(OFF LINE)= | | | | | | 23.6 | |
| 13 | | | | | | | | |
| 14 | | | | | | | ON LINE | OFF LINE |
| 15 | | SUM ETALON ABSORPTION= | | | | | 4.95E-03 | 2.09E-04 |
| 16 | | FRACTION ETALON ABS= | | | | | 3.50E-04 | 1.48E-05 |
| 17 | | | | | | | | |
| 18 | FREQUENCY | LINESTRENG | ETALON TRANSMISSION | | | | ETALON GAS TRANSMISSION | |
| 19 | (cm-1) | | ON LINE | OFF LINE | | | ON LINE | OFF LINE |
| 151 | | | 0.000 | 0.000 | | | 0.00E+00 | 0.00E+00 |
| 152 | 2979.0115 | 1.22E-19 | 0.886 | 0.035 | | | 2.90E-04 | 1.13E-05 |
| 153 | 2978.9197 | 7.32E-20 | 0.960 | 0.034 | | | 1.88E-04 | 6.69E-06 |
| 154 | 2978.8479 | 4.88E-20 | 0.993 | 0.034 | | | 1.30E-04 | 4.40E-06 |
| 155 | 2978.6504 | 7.27E-20 | 0.939 | 0.033 | | | 1.83E-04 | 6.36E-06 |
| 156 | | | 0.000 | 0.000 | | | 0.00E+00 | 0.00E+00 |
| 157 | 2968.8550 | 7.21E-20 | 0.733 | 0.036 | | | 1.42E-04 | 6.92E-06 |
| 158 | 2968.7361 | 7.21E-20 | 0.861 | 0.035 | | | 1.66E-04 | 6.74E-06 |
| 159 | 2968.4734 | 4.74E-20 | 0.998 | 0.033 | | | 1.27E-04 | 4.22E-06 |
| 160 | 2968.4034 | 7.14E-20 | 0.974 | 0.033 | | | 1.86E-04 | 6.30E-06 |
| 161 | | | 0.000 | 0.000 | | | 0.00E+00 | 0.00E+00 |
| 162 | 2968.5824 | 4.27E-20 | 0.599 | 0.037 | | | 6.86E-05 | 4.23E-06 |
| 163 | 2958.6509 | 6.39E-20 | 0.631 | 0.037 | | | 1.08E-04 | 6.28E-06 |
| 164 | 2958.5362 | 1.07E-19 | 0.754 | 0.036 | | | 2.16E-04 | 1.02E-05 |
| 165 | 2958.2327 | 6.28E-20 | 0.997 | 0.034 | | | 1.68E-04 | 5.65E-06 |
| 166 | 2958.1199 | 6.32E-20 | 0.982 | 0.033 | | | 1.56E-04 | 5.59E-06 |
| 167 | 2958.0171 | 1.06E-19 | 0.912 | 0.033 | | | 2.59E-04 | 9.24E-06 |
| 168 | | | 0.000 | 0.000 | | | 0.00E+00 | 0.00E+00 |
| 169 | 2948.4739 | 5.24E-20 | 0.515 | 0.038 | | | 7.23E-05 | 5.32E-06 |
| 170 | 2948.4214 | ?.22E-20 | 0.562 | 0.037 | | | 7.86E-05 | 5.22E-06 |
| 171 | 2948.1077 | 8.51E-20 | 0.889 | 0.035 | | | 2.03E-04 | 7.91E-06 |
| 172 | 2947.9121 | 5.12E-20 | 1.000 | 0.033 | | | 1.37E-04 | 4.59E-06 |
| 173 | 2947.8111 | 3.43E-20 | 0.978 | 0.033 | | | 8.99E-05 | 3.03E-06 |
| 174 | 2947.5682 | 5.16E-20 | 0.866 | 0.032 | | | 1.20E-04 | 4.47E-06 |
| 175 | | | 0.000 | 0.000 | | | 0.00E+00 | 0.00E+00 |
| 176 | 2937.2520 | 6.63E-20 | 0.741 | 0.032 | | | 1.32E-04 | 5.67E-06 |
| 177 | 2938.2151 | 3.97E-20 | 0.480 | 0.038 | | | 5.11E | |
| 178 | 29381922 | 2.64E-20 | 0.499 | 0.038 | | | | |
| | 2937.7671 | 3.86E-20 | 0.925 | | | | | |
| | | 3.89E-20 | 0.000 | | | | | |

ETALON DESIGN FOR METHANE (R-BRANCH) DETECTION IN THE PRESENCE OF WATER.

| | A | B | C | D | E | F | G | H | I | J |
|---|---|---|---|---|---|---|---|---|---|---|
| 1 | COMBINED INPUT/OUTPUT SHEET FOR ETHANE AND METHANE | | | | | | | | | |
| 2 | INPUT PARAMETERS: | | | | REFLECTIVE ETALON | | | | | |
| 3 | FREQUENCY: | | | | ETALON REFLECTIVITY (%) | | 80 | | | |
| 4 | CENTER (cm−1) = | | 3085.9 | | FREE SPEC RANGE (cm−1) | | 9.32 | | | |
| 5 | UPPER LIMIT (cm−1) = | | 3110 | | | | | | | |
| 6 | LOWER LIMIT (cm−1) = | | 3060 | | | | | | | |
| 7 | MODULATION(% OF RANGE) | | 53 | | | | | | | |
| 8 | TOTAL INTENSITY IN WINDOW(cm−1) = | | | | | 50.00 | | | | |
| 9 | INTENSITY TRANSMITTED BY ETALON(cm−1) = | | | | | 5.56 | | | | |
| 10 | | | | | | | | | | |
| 11 | | | | | | | | | | |
| 12 | | | | | ETHANE | | METHANE | | WATER | |
| 13 | GAS CONC (ppm x cm)= | | | | 0 | | 100 | | 2300000 | |
| 14 | | | | | ON LINE | OFF LINE | ON LINE | OFF LINE | ON LINE | OFF LINE |
| 15 | SUM ETALON ABSORPTION= | | | | 0.00E+00 | 0.00E+00 | 6.01E-03 | 8.07E-05 | 6.90E-02 | 6.84E-02 |
| 16 | FRACTION ETALON ABS= | | | | 0.00E+00 | 0.00E+00 | 1.08E-03 | 1.45E-05 | 1.24E-02 | 1.23E-02 |
| 17 | RATIO ABSORPTION= | | | | #DIV/0! | | 74.53 | | 1.01 | |
| 18 | (ON LINE)/(OFF LINE) | | | | | | | | | |
| 19 | SIGNAL STRENGTH | | | | 0.00E+00 | | 5.93E-03 | | 5.78E-04 | |

| | A | B | C | D | E | F | G | H | I | J |
|---|---|---|---|---|---|---|---|---|---|---|
| | ETALON DESIGN FOR ETHANE DETECTION AT 3.3 μm IN THE PRESENCE OF METHANE AND WATER. | | | | | | | | | |
| 1 | COMBINED INPUT/OUTPUT SHEET FOR ETHANE AND METHANE | | | | | | | | | |
| 2 | INPUT PARAMETERS: | | | | | | | | | |
| 3 | FREQUENCY: | | | | REFLECTIVE ETALON | | | | | |
| 4 | CENTER (cm-1) = | | 2983.4 | | ETALON REFLECTIVITY (%) | | 80 | | | |
| 5 | UPPER LIMIT (cm-1) = | | 3000 | | FREE SPEC RANGE (cm-1) | | 6.7 | | | |
| 6 | LOWER LIMIT (cm-1) = | | 2962 | | | | | | | |
| 7 | MODULATION(% OF RANGE) | | -7 | | | | | | | |
| 8 | TOTAL INTENSITY IN WINDOW(cm-1) = | | | | | 38.00 | | | | |
| 9 | INTENSITY TRANSMITTED BY ETALON(cm-1) = | | | | | 4.22 | | | | |
| 10 | | | | | | | | | | |
| 11 | | | | | | | | | | |
| 12 | | | | | ETHANE | | METHANE | | WATER | |
| 13 | GAS CONC (ppm x cm)= | | | | 100 | | 10000 | | 2300000 | |
| 14 | | | | | ON LINE | OFF LINE | ON LINE | OFF LINE | ON LINE | OFF LINE |
| 15 | SUM ETALON ABSORPTION= | | | | 2.38E-03 | 1.04E-03 | 6.99E-03 | 5.61E-05 | 3.68E-03 | 4.57E-03 |
| 16 | FRACTION ETALON ABS= | | | | 5.64E-04 | 2.47E-04 | 1.66E-03 | 1.33E-05 | 8.71E-04 | 1.08E-03 |
| 17 | RATIO ABSORPTION= | | | | 2.28 | | 1.25 | | 0.80 | |
| 18 | (ON LINE)/(OFF LINE) | | | | | | | | | |
| 19 | SIGNAL STRENGTH | | | | 1.34E-03 | | 1.38E-03 | | -8.98E-04 | |

FIG.16

| | A | B | C | D | E | F | G | H | I | J |
|---|---|---|---|---|---|---|---|---|---|---|
| | ETALON DESIGN FOR METHANE (P-BRANCH) DETECTION AT 3.3 μm IN THE PRESENCE OF WATER. | | | | | | | | | |
| 1 | COMBINED INPUT/OUTPUT SHEET FOR ETHANE AND METHANE | | | | | | | | | |
| 2 | INPUT PARAMETERS: | | | | REFLECTIVE ETALON | | | | | |
| 3 | FREQUENCY: | | | | ETALON REFLECTIVITY (%) | | 70 | | | |
| 4 | CENTER (cm-1) = | | 2958.2 | | FREE SPEC RANGE (cm-1) | | 10.3 | | | |
| 5 | UPPER LIMIT (cm-1) = | | 2990 | | | | | | | |
| 6 | LOWER LIMIT (cm-1) = | | 2910 | | | | | | | |
| 7 | MODULATION(% OF RANGE) | | 58.5 | | | | | | | |
| 8 | TOTAL INTENSITY IN WINDOW(cm-1) = | | | | | 80.00 | | | | |
| 9 | INTENSITY TRANSMITTED BY ETALON(cm-1) = | | | | | 14.12 | | | | |
| 10 | | | | | | | | | | |
| 11 | | | | | | | | | | |
| 12 | | | | | ETHANE | | METHANE | | WATER | |
| 13 | GAS CONC (ppm x cm)= | | | | 0 | | 100 | | 2300000 | |
| 14 | | | | | ON LINE | OFF LINE | ON LINE | OFF LINE | ON LINE | OFF LINE |
| 15 | SUM ETALON ABSORPTION= | | | | 0.00E+00 | 0.00E+00 | 4.95E-03 | 2.09E-04 | 1.94E-02 | 1.94E-02 |
| 16 | FRACTION ETALON ABS= | | | | 0.00E+00 | 0.00E+00 | 3.50E-04 | 1.48E-05 | 1.37E-03 | 1.38E-03 |
| 17 | RATIO ABSORPTION= | | | | #DIV/0! | | 23.65 | | 1.00 | |
| 18 | (ON LINE)/(OFF LINE) | | | | | | | | | |
| 19 | SIGNAL STRENGTH | | | | 0.00E+00 | | 4.74E-03 | | -6.06E-05 | |

ETALON DESIGN FOR METHANE DETECTION AT 1.6 μm IN THE PRESENCE OF WATER.

|  | A | B | C | D | E | F | G | H | I | J |
|---|---|---|---|---|---|---|---|---|---|---|
| 1 | COMBINED INPUT/OUTPUT SHEET FOR ETHANE AND METHANE | | | | | | | | | |
| 2 | INPUT PARAMETERS: | | | | REFLECTIVE ETALON | | | | | |
| 3 | FREQUENCY: | | | | ETALON REFLECTIVITY (%) | | 80 | | | |
| 4 | CENTER (cm-1) = | | 6067.1 | | FREE SPEC RANGE (cm-1) | | 9.83 | | | |
| 5 | UPPER LIMIT (cm-1) = | | 6107 | | | | | | | |
| 6 | LOWER LIMIT (cm-1) = | | 6057 | | | | | | | |
| 7 | MODULATION(% OF RANGE) | | 51.5 | | | | | | | |
| 8 | TOTAL INTENSITY IN WINDOW(cm-1) = | | | | | 50.00 | | | | |
| 9 | INTENSITY TRANSMITTED BY ETALON(cm-1) = | | | | | 5.56 | | | | |
| 10 | | | | | | | | | | |
| 11 | | | | | | | | | | |
| 12 | | | | | ETHANE | | METHANE | | WATER | |
| 13 | GAS CONC (ppm x cm)= | | | | 0 | | 100 | | 2300000 | |
| 14 | | | | | ON LINE | OFF LINE | ON LINE | OFF LINE | ON LINE | OFF LINE |
| 15 | SUM ETALON ABSORPTION= | | | | 0.00E+00 | 0.00E+00 | 4.03E-05 | 5.91E-07 | 1.54E-05 | 1.52E-05 |
| 16 | FRACTION ETALON ABS= | | | | 0.00E+00 | 0.00E+00 | 7.25E-06 | 1.06E-07 | 2.78E-06 | 2.73E-06 |
| 17 | RATIO ABSORPTION= | | | | #DIV/01 | | 68.14 | | 1.02 | |
| 18 | (ON LINE)/(OFF LINE) | | | | | | | | | |
| 19 | SIGNAL STRENGTH | | | | 0.00E+00 | | 3.97E-05 | | 2.50E-07 | |

NATURAL GAS DETECTION APPARATUS AND METHOD OPERABLE IN A MOVING VEHICLE

CROSS-REFERENCE TO RELATED APPLICATIONS

This application claims the benefit of U.S. Provisional Application No. 60/013,079, filed Mar. 8, 1996.

STATEMENT REGARDING FEDERALLY SPONSORED RESEARCH OR DEVELOPMENT

Not Applicable

BACKGROUND OF THE INVENTION

The following invention relates generally to a natural gas detection apparatus and method, and in particular to an optical natural gas detector for mounting on a natural gas leak survey vehicle.

By federal regulation, the natural gas industry must periodically survey the entire natural gas distribution network for leaks. Currently, the network includes approximately 1.59 million miles of underground pipeline. This vast network of underground natural gas pipeline must be surveyed by natural gas personnel either on foot or by vehicle.

Natural gas personnel face significant obstacles when surveying for underground gas leaks. An effective gas detection device must effectively and economically overcome these obstacles.

First, before being detectable, the gas must filter up through the soil. If the gas pipeline is buried beneath a street, sidewalk, or parking lot, the gas must also filter up through pavement. After filtering up through the ground and pavement, the gas is quickly dispersed by wind. Accordingly, a gas detection device must be extremely sensitive. To detect a natural gas leak under these conditions, a gas detection device should be able to detect trace quantities of gas as low as 1 part per million (ppm).

Second, in addition to wind, a gas detection device must be able to detect gas leaks under varied and extreme environmental conditions. In addition to detecting natural gas in rain, snow, heat, dust, or humidity, the detection device itself must be able to withstand variations in temperature and humidity. Therefore, the device must be rugged and operable under a variety of weather conditions. Although extremely sensitive gas detection devices have proven effective in the confines of the laboratory, these sensitive but fragile devices have not previously been adapted to the field.

Also, although some prior art gas detection devices have been adapted to hostile external environments, these devices have faced static environmental conditions. For example, gas detection devices have been developed to detect emissions from a smokestack or gas levels in a factory. These devices are designed for a specific environment and do not face extreme variations in both temperature and humidity.

Third, unlike laboratory and static environment gas detectors, an effective natural gas detector must be mobile. A natural gas detector must go to the gas, rather than vice versa. More importantly, the gas detection device must be effective when moving very quickly. As previously noted, millions of miles of underground gas pipeline must regularly be surveyed. To cost effectively survey this vast length of pipeline for leaks, a gas detection device must be able to detect trace quantities of gas while being moved very quickly over the pipelines. Because much of the underground natural gas network is located beneath streets, these pipelines are most effectively surveyed by a gas detector mounted on a vehicle.

Currently, natural gas personnel survey over 100,000 miles of gas pipeline by vehicle using a flame ionization unit (FIU). The FIU is mounted on leak survey vehicles. The FIU employs a manifold of sample intake ports, generally located below the front bumper of the vehicle and extending from wheel to wheel. The ports direct samples of air to the FIU sensor. The FIU sensor includes a hydrogen-air flame that creates chemiions from any combustible or oxidizable substance in the intake air including, but not limited to, natural gas. The flame is flanked by two electrodes that collect the ions, resulting in a current. After being suitably amplified, the current is fed to a meter readout and audio alarm.

Although the FIU detector may detect trace quantities of natural gas, the FIU is ineffective at higher vehicle speeds. The leak survey vehicle must travel at a speed from 2–7 miles per hour, depending on the level of sensitivity desired. Typically, for the required sensitivity, the vehicle must travel at approximately 2–3 miles per hour.

Obviously, the productivity of this system is poor. Personnel typically may survey only 5–10 miles per day. In addition, the slow vehicle speed typically disrupts traffic and engenders ill will towards natural gas personnel.

Also, the FIU detector system suffers from a slow response time. The FIU detector system must collect a sample of air, direct the air to the flame, burn any combustibles in the air, and then analyze the ions. Only then is an operator alerted to the presence of a natural gas leak. After the operator is alerted, the vehicle must retrace its path or use alternative detection methods to find the precise location of the offending gas leak. Moreover, because the FIU responds to all combustible substances, the FIU often endures false positive readings.

Accordingly, those skilled in the art of natural gas detection have sought a method and device for detecting natural gas that is highly sensitive, rugged, operable under varied and extreme environmental conditions, mobile, able to be mounted on a vehicle and operated at relatively high vehicle speeds, cost effective, immediately responsive to natural gas leaks, and resistant to false positive readings.

BRIEF SUMMARY OF THE INVENTION

A natural gas detector based on optical etalon technology is disclosed. The detector may be mounted on a natural gas survey vehicle. The detector uses an etalon that operates at an optimum set of wavelengths for detecting natural gas. This optimum set of wavelengths is disclosed, along with alternative sets of wavelengths.

To this end, a natural gas detection system is provided for use with a vehicle. A natural gas detector apparatus is mounted to the vehicle so that the vehicle transports the detector apparatus over an are of interest at speeds of up to 20 miles per hour. The detector apparatus includes a transmitter section and a receiver section displaced a preselected distance from each other. The transmitter section has a light source transmitting a light beam to the receiver section forming a beam path therebetween. The apparatus is arranged such that natural gas intercepts the beam path and absorbs representative wavelengths of the light beam. The receiver section receives a portion of the light beam onto an electro-optical etalon for detecting the gas.

A method of detecting natural gas is also provided. The method has the steps of providing a vehicle and mounting a natural gas detector apparatus to the vehicle. The detector apparatus has a transmitter section and a receiver section displaced a preselected distance from each other. The transmitter section includes a light source. The method includes transmitting a light beam in a beam path from the transmitter section to the receiver section, and driving the vehicle over an area of interest so that natural gas intercepts the beam path and absorbs representative wavelengths of the light beam. The method also includes receiving a portion of the light beam in the receiver section so that the light beam is directed into an etalon, and detecting a gas leak in the area of interest from the portion light beam using the gas detection apparatus mounted on the vehicle while the vehicle is in motion.

In view of the problems in the art discussed above, an advantage of the present invention is to provide a highly sensitive natural gas detector that is capable of detecting trace quantities of natural gas.

An additional advantage of the present invention is to provide a rugged natural gas detector that reliably operates in the field under a variety of environmental conditions.

A further advantage of the present invention is to provide a mobile natural gas detector that may be mounted on a natural gas leak survey and operated at a vehicle speed of at least 20 mph.

Yet another advantage of the present invention is to provide a cost effective natural gas detector constructed of the most economical materials.

A still further advantage of the present invention is to provide a natural gas detector that is immediately responsive to the presence of a natural gas leak.

Finally, an advantage of the present invention is to provide a discriminating natural gas detector that is resistant to false positive readings.

BRIEF DESCRIPTION OF THE SEVERAL VIEWS OF THE DRAWING

FIG. 14 is a table of data showing a sample spreadsheet for calculating performance of methane detecting reflective etalon;

FIG. 15 is a table showing etalon design for methane (R-branch) detection in the presence of water;

FIG. 16 is a table showing etalon design for methane detection at 3.3 µm in the presence of methane and water;

FIG. 17 is a table showing etalon design for methane (P-branch) detection at 3.3 µm in the presence of water; and FIG. 18 is a table showing etalon design for methane detection at 1.6 µm in the presence of water.

DETAILED DESCRIPTION OF THE INVENTION

Although the invention is described in connection with one or more preferred embodiments, the invention is not limited to those embodiments. The invention includes alternatives, modifications, and equivalents that are included in the spirit and scope of the intended claims.

The natural gas leak detector of the present invention utilizes a light source and an optical etalon filter to detect the presence and measure the concentration of either methane or ethane in a path of light. If a gas leak occurs, the gas will filter up from the leak and into the air. When the light beam crosses the plume of escaping gas, the system will detect the natural gas in the detection area and measure its concentration. The system utilizes spectroscopic techniques, as will be described, to analyze the light beam.

Figure 1:
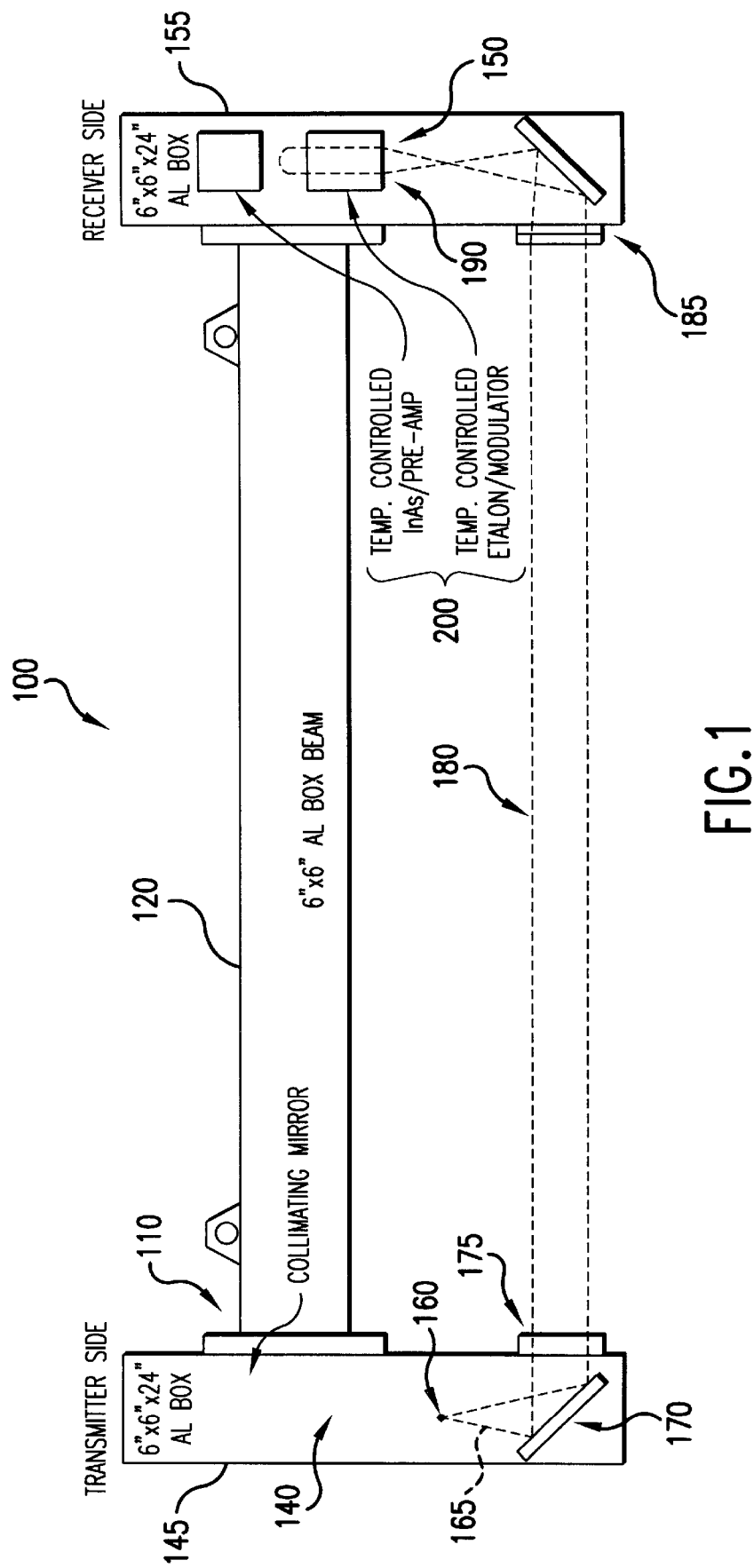
FIG. 1 is a front diagrammatic view of the optical natural gas detector of the present invention.
Figure 2:
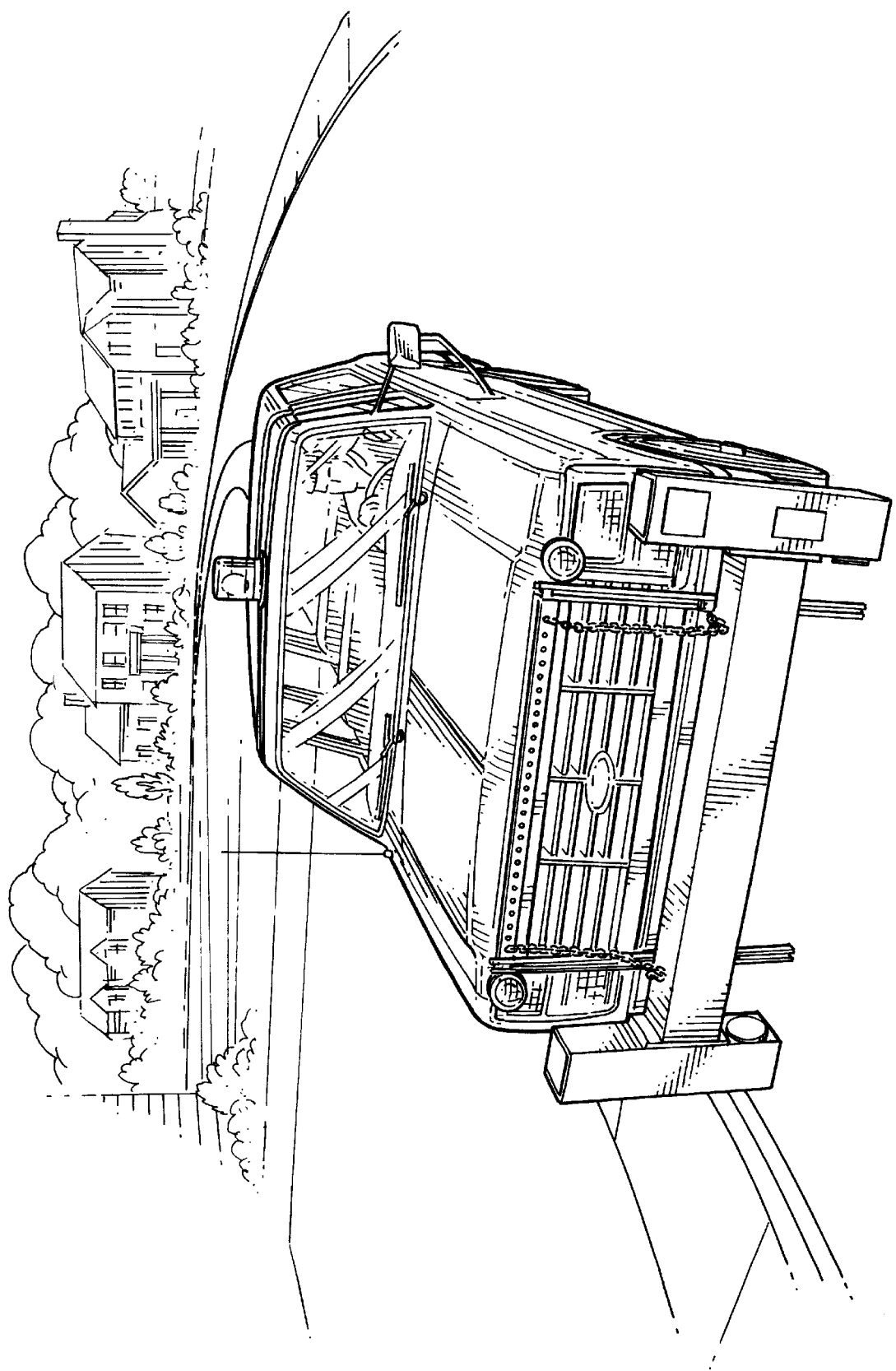
FIG. 2 is a photographic image of the optical natural gas detector mounted on a natural gas leak survey vehicle.

An embodiment of a detector system indicated generally at 100 in FIG. 1 is comprised of durable and rugged solid state components that are operable under varied and extreme environmental conditions. The system can measure gas concentrations at frequencies up to several kilohertz. Accordingly, when mounted on a vehicle 105, as shown in FIG. 2, the system may detect trace quantities of gas at high vehicle operating speeds. An embodiment of the system 100 has reliably detected gas concentrations as low as 1 ppm at vehicle speeds in excess of 20 miles per hour.

Referring to FIG. 1, a housing 110 of the prototype natural gas detector system 100 is constructed of aluminum U-channel. A more compact housing for the present invention has been constructed. It is also anticipated that a production model of the present invention may employ a substantially different structure for the housing. However, all structures provide a detection path for detecting natural gas and any variations on the structure do not affect the novel aspects of the present invention.

In the prototype, the U-channel used in the housing 110 is 6 inches wide with 3 inch sides and ¼ inch thick walls. To construct a central box beam 120, two U-channels are welded together to create an approximately 5 foot long box beam 120. The box beam 120 connects a transmitter 140 and a receiver 150. Transmitter and receiver housings 145, 155 are also constructed of two welded U-channels and are bolted to the box beam 120 with ½ inch thick flanges. The transmitter and receiver housings 145, 155 are each 24 inches long. Because the disclosed housing structure 110 is larger and heavier than required, it is anticipated that a production model may employ a substantially different structure for the housing 110.

On the transmitter housing section 145, a tungsten halogen light source 160, preferably a tungsten halogen light source, transmits a light beam 165 downward to a reflecting mirror 170. The mirror 170 reflects the beam 165 through a fused silica window 175 and across an approximately five-foot detection beam path 180 to the receiver housing section 155. As can be seen from FIGS. 1 and 2, the beam path 180 is exposed to the environment, and not enclosed in a sample cell as in known gas detectors.

At the receiver housing section 155, a lens 185, preferably a Fresnel lens, collimates the light beam 165 into an approximately four-inch diameter beam 190. The beam 190 is reflected upward and focused on a temperature-controlled filter assembly 200 including an entrance polarizer, a modulator, an etalon, and an exit polarizer (see also FIGS. 10 and 11). The filter assembly 200 also includes a fused silica lens 210 that recollimates the beam 190 to match the aperture of the etalon filter and modulator. The filter assembly 200 focuses the beam on a thermo-electrically cooled optical detector 215. As previously mentioned, the spectroscopic technique of the filter assembly 200 will be described in more detail.

It is anticipated that a system with a smaller diameter beam would be equally effective and less expensive to produce. However, the relatively large four-inch diameter beam 190 offers certain advantages. With a large diameter beam, the sensor is relatively insensitive to debris or insects that may pass through the beam or adhere to the windows. Also, the transmission and receiver components are difficult to maintain in precise alignment and the light beam may move relative to the receiver. The large diameter light beam 190 negates this problem because the beam sufficiently overlaps the optical detector to make relative movement of the beam inconsequential.

Figure 3:
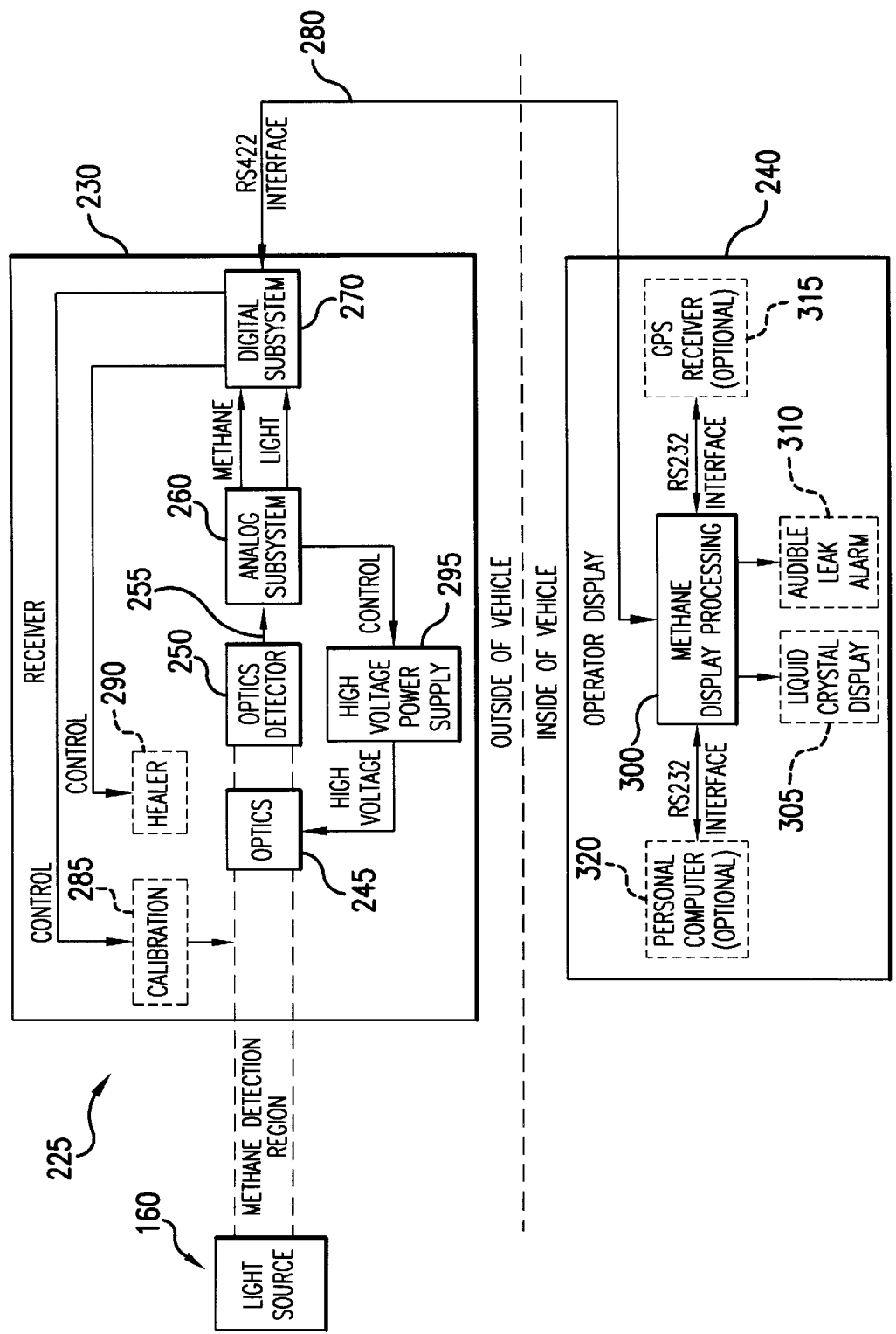
FIG. 3 is a schematic diagram of the optical detector and the electrical control and data processing system of the present invention.

The system electronics are diagrammed and referenced 225 in FIG. 3. The system electronics 225 include a receiver section 230 located outside the vehicle 105 (see FIG. 2) and an operator display section 240 located inside the vehicle. The light source 160 (see FIG. 1) provides an optical input through optics referenced 245 to an optical detector 250. The optical detector 250 converts the optical signal to an electrical signal 255 that is transmitted to an analog subsystem 260. The analog subsystem 260 amplifies the signal and transmits it to a digital subsystem 220. The digital subsystem 270 converts the amplified analog signal to a digital signal. The signal is then transmitted via a communication link 280, for example an RS-422 interface, to the operator display 240 inside the survey vehicle.

The system electronics 225 also include controls for a calibration unit 285, a heater unit 290, and a high voltage power supply 295. The calibration unit 285 may supply a cell of methane to the detection path 180 for calibrating the system. The heater unit 290 controls the temperature of optical components. The high voltage power supply 295 modulates a filter system, as will be described. The communication link 280 transmits the digital signal to a display data processor 300 in the operator display 240. The operator display 240 also includes peripherals connected to the data processor 300. The peripherals include a liquid crystal display 305, an audible alarm 310, a GPS receiver 315 and a personal computer 320.

Because the modulator preferably operates at a frequency of 14 kilohertz, the optical technology is sampling the detection path for natural gas at a higher frequency than the electronic technology can process. Accordingly, the signal may be integrated over a number of cycles.

In field tests, the signal has been integrated over 140 cycles (10 msec) and 1400 cycles (100 msec). By integrating the signals, the effect of anomalous signals is greatly reduced and system noise is suppressed. This increases the sensitivity of the system. Although the response time of the system suffers, the resolution is sufficient for locating a natural gas leak. A vehicle operating at 20 mph moves 10 cm in 10 msec and 1 meter in 100 msec. Because a precision of 1 meter is sufficient for locating a gas leak, a 100 msec integration time does not detrimentally affect the system resolution.

Figure 4:
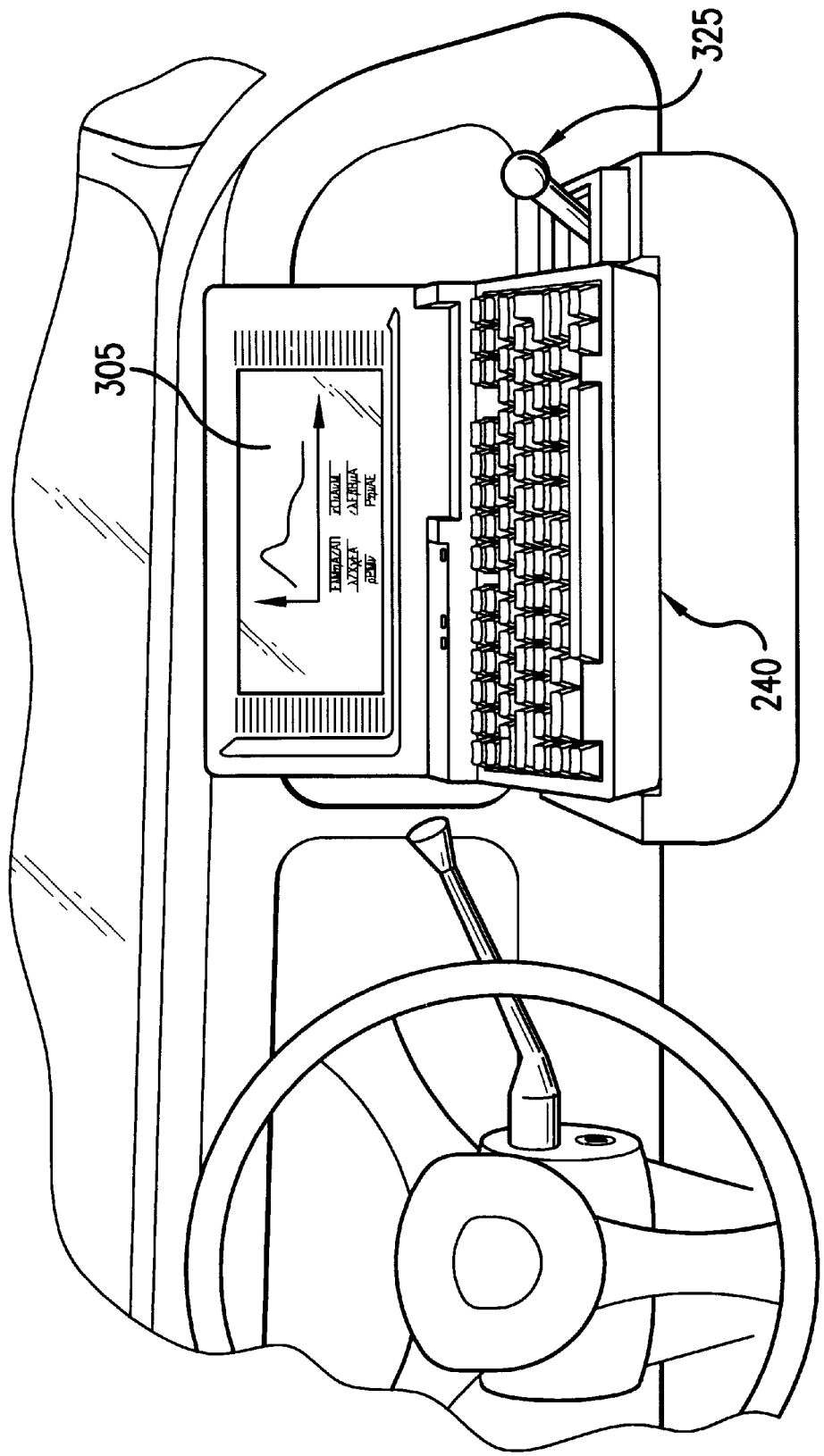
FIG. 4 is a drawing of the operator interface for the natural gas detector of the present invention.

As shown in FIG. 4, the data may be displayed inside the survey vehicle 105 and monitored by an operator using the operator display 240. If natural gas is detected, the display 240 indicates the concentration of the gas and the controller may sound the alarm 310. The controller may also receive information from the vehicle's odometer to permit the graphing of gas concentration over the distance traveled on the LCD 305. Alternatively, the gas concentration may be graphed over time. A sensor head position control 325 is also provided inside the vehicle for remotely controlling the detector system 100.

As can be seen from the general description of the gas detection system, the system may immediately detect the presence and concentration of a natural gas leak. Unlike the prior art FIU detector system, which must collect and remotely analyze an air sample, the present system may detect natural gas instantly and plot the concentration of the gas over time and/or distance. Also, because the system utilizes optical signal absorption technology, the system may measure gas concentrations at frequencies up to several kilohertz. This high sampling rate allows the vehicle to travel at up to 20 miles per hour without sacrificing sensitivity.

The gas detection system 100 of the present invention utilizes spectroscopic technology to detect the presence of natural gas in a light beam. Referring to FIG. 1, to determine if a specific gas is present in a detection area, a light beam may be directed through the detection area. When the light beam passes through the gas, the gas absorbs specific wavelengths of the light. By analyzing the light beam after it has passed through the detection area, the gas may be detected. Also, by measuring the amount of light absorbed, the concentration of the gas may be determined.

Figure 5:
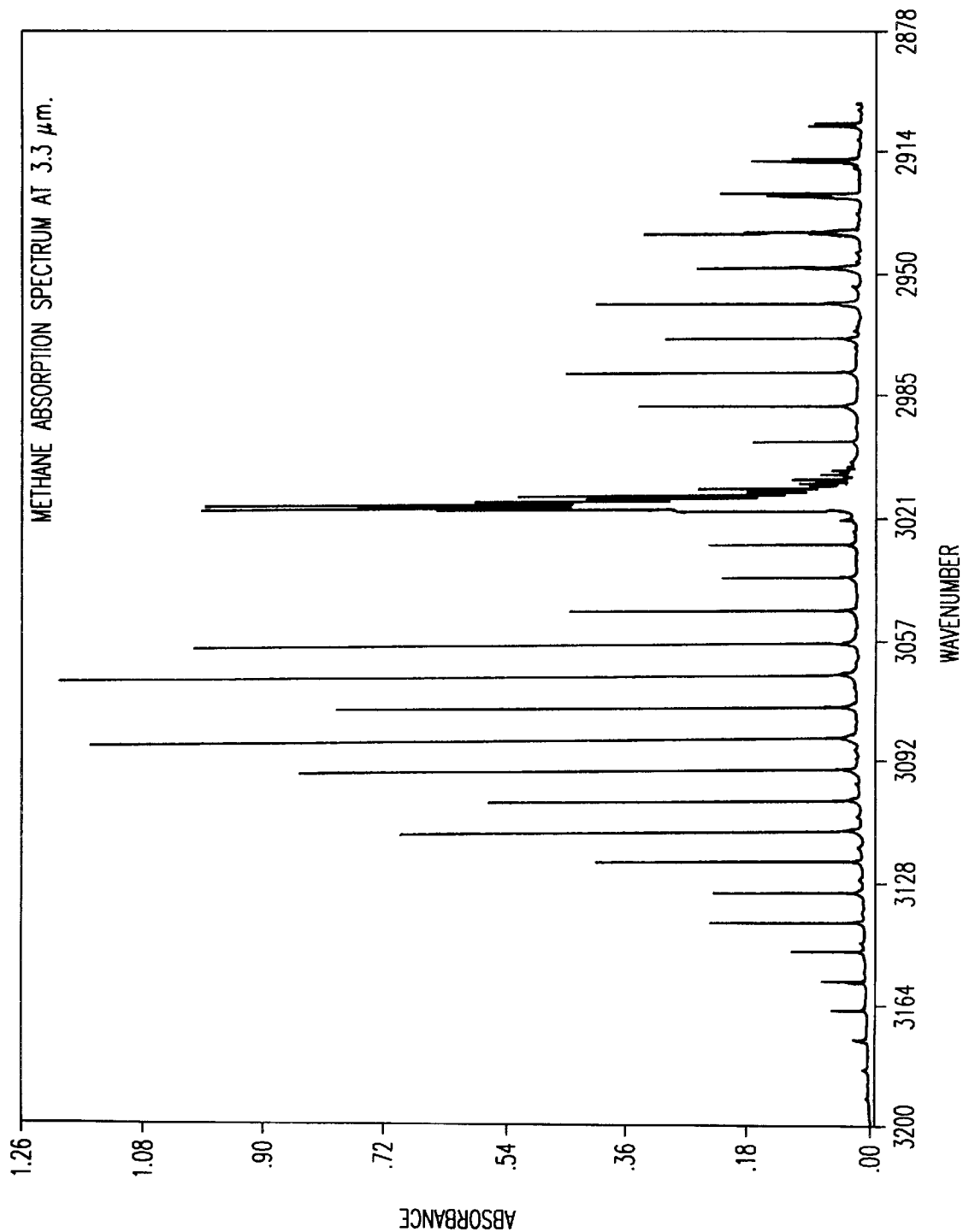
FIG. 5 is a graph of the absorption line spectrum for methane at 3.3 µm.

Every molecular gas absorbs a characteristic set of wavelengths, or spectrum, of light. This absorption spectrum, also known as absorption lines, may be plotted. For example, the absorption spectrum at 3.3 $\mu$m for methane is shown in FIG. 5. At this wavelength, methane exhibits a series of very sharp absorption lines that are very regularly spaced due to the vibrational-rotational energy levels of the gas. If a light beam is directed through methane, the methane will absorb the wavelengths of light that match the absorption lines shown in FIG. 5.

Figure 6A:
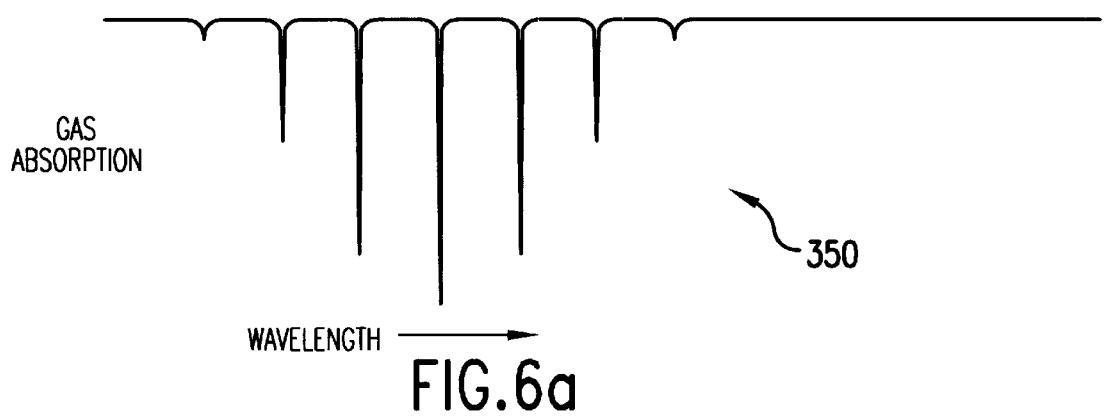
FIGS. 6a–c is a set of graphs explaining a conventional optical method for detecting a gas.
Figure 6B:
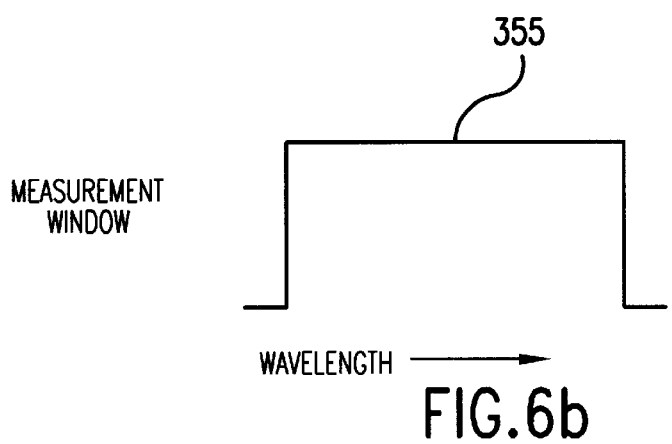
Figure 6C:
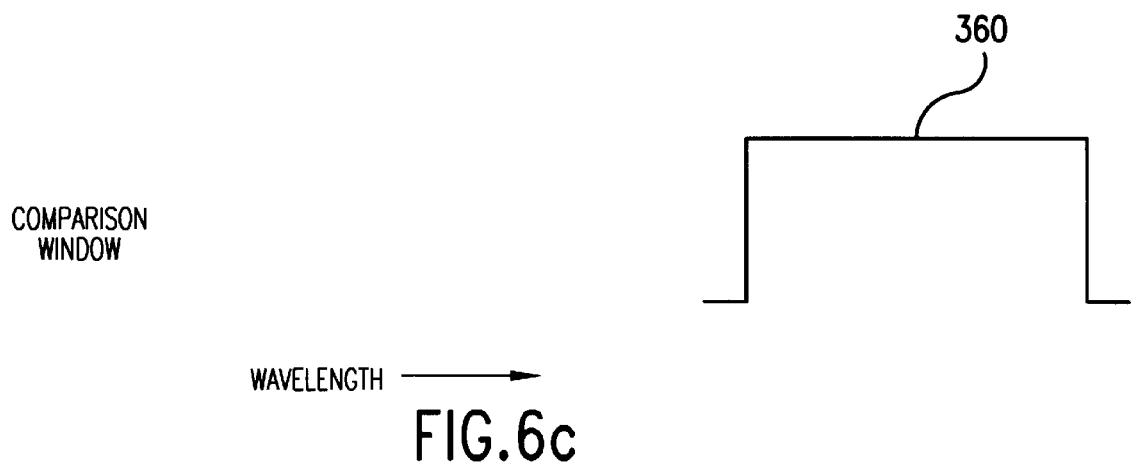

FIGS. 6a–c describe one method of detecting and measuring the concentration of a gas with a known absorption spectrum. In FIG. 6a, a light has been directed through a gas. The gas has absorbed a characteristic spectrum 350 at specific wavelengths. To detect this absorption, a specific wavelength range of the light may be measured. The wavelength range may be isolated through the use of interference filters and other devices as will be described herein.

As shown in FIG. 6b, an isolated wavelength range, or measurement window 355, is centered on the absorption lines of the gas to be measured. The measurement window is selected to correlate with the spectrum lines 350 of the gas of interest. To determine the light absorbed, the light transmission in the measurement window 355 must be compared to the light transmission where little or no absorption occurs. Therefore, a comparison must be made with a reference window 360. The reference window 360 is shown in FIG.

6c. The reference window 360 is selected so that it does not correlate with the spectrum lines of the gas of interest.

In the system represented in FIGS. 6a–c, the light beam may be modulated from the measurement window 355 to the reference window 360. The modulated light beam is directed to an optical sensor that measures light transmission. When modulated with no gas present in the detection area, the light transmission in the measurement and transmission windows will be roughly the same. However, when a gas enters the detection area, the light transmission in the measurement window 355 will decrease in comparison to the light transmission in the reference window 360. The drop in transmission in the measurement window 355 indicates that the gas is present in the detection area. The concentration of the gas may be determined by comparing the transmission of light in the two wavelength ranges.

The system represented in FIG. 6, however, is not the optimum system for detecting and measuring a gas. First, a gas will absorb very little of the total energy present in the correlation wavelength range. The width of a single methane absorption line, for example, is approximately 0.1 cm$^{-1}$ FWHM (full width at half maximum) at standard temperature and pressure. The separation between the absorption lines is approximately 10 cm$^{-1}$. As a result, only 1 percent of the wavelength range is capable of being absorbed by methane. Therefore, the presence of methane in the detection area causes very little difference in the light transmission in the measurement and reference windows. This makes detection difficult.

Second, the measurement and reference windows must be widely separated in wavelength so that the reference window 360 avoids the absorption spectrum 350 of the gas to be detected. For methane, the measurement and reference windows must be separated by about 300 cm$^{-1}$. At this relatively large distance, the transmission strength may vary between the two wavelengths for reasons unrelated to the presence of a gas. This causes false signals.

Third, other gases in particular water vapor, typically have absorption lines in both the measurement and reference windows. These lines are difficult to avoid with a broad transmission band. Thus, other gases may cause false signals and otherwise generate interference.

Finally, optical devices cannot easily modulate between the separated wavelengths at a sufficiently high frequency to detect trace amounts of gas. This limitation is especially apparent when the gas detection system is moving. If the detection device does not modulate at a sufficiently high frequency, the moving detector may pass over a gas leak before the detector completes a modulation cycle. In that event, the gas leak will be missed. Alternatively, the survey vehicle must be driven at a slow speed to accommodate the low frequency detection cycle.

Figure 7A:
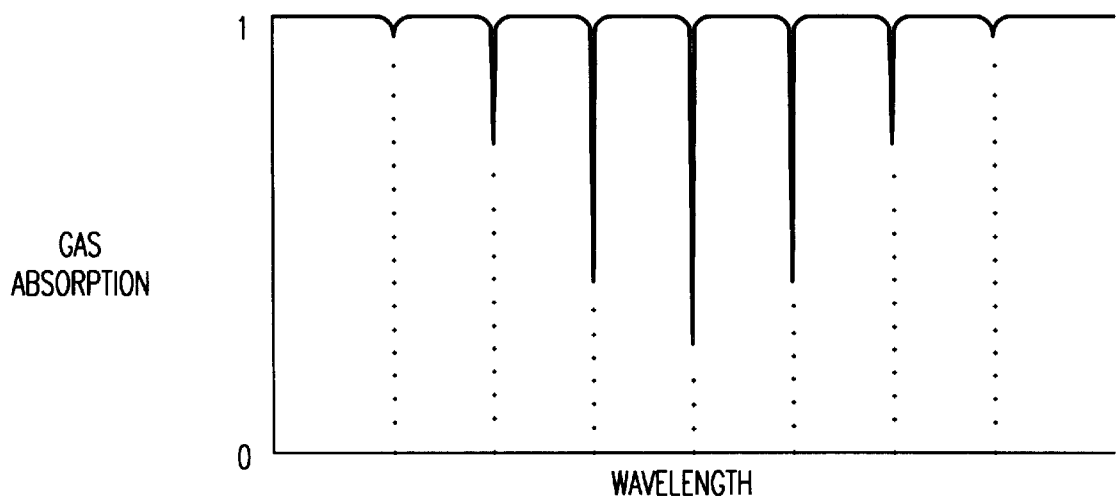
FIGS. 7a–c is a set of graphs explaining, an optical method for detecting a gas that uses an etalon.
Figure 7B:
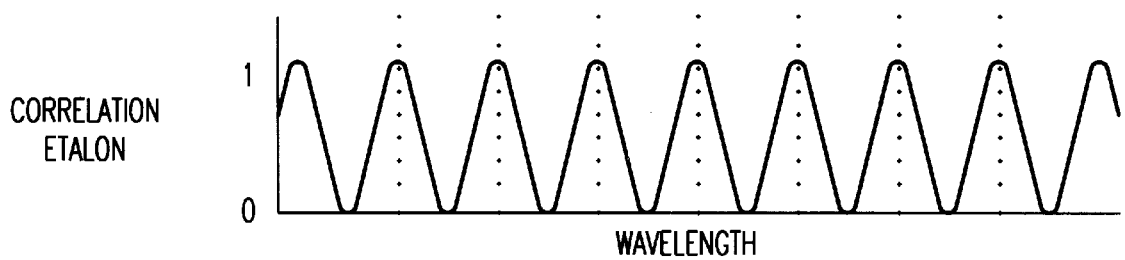

To overcome these problems, the present invention utilizes an electro-optical etalon for differential gas absorption measurements. Rather than transmitting a broad band of light, the etalon operates as a filter and periodically transmits a series of wavelength bands of light. The design of the etalon controls the spacing and the width of the bands. The spacing and width of the transmitted bands may be specifically correlated to the absorption lines of a specific gas. As shown in FIG. 7b, rather than a broad measurement window, the etalon generates periodic wavelengths of light. The wavelengths correlate with the absorption lines of a specific gas. shown in FIG. 7a.

Figure 7C:
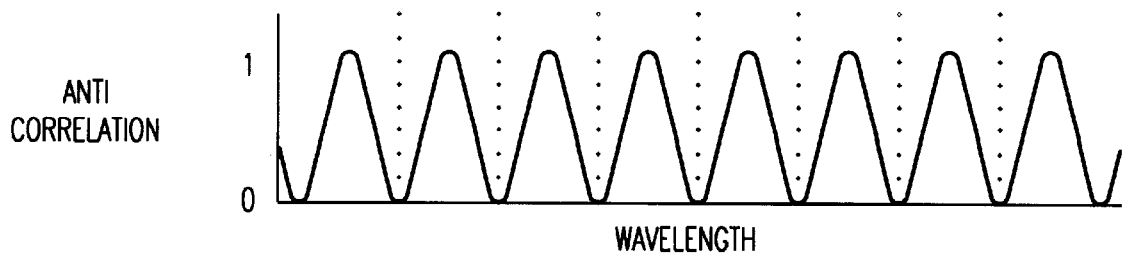

To provide a reference or anti-correlation measurement, the periodic wavelengths of light may be moved between the absorption lines of the gas, as shown in FIG. 7c. Because the gas is not absorbing at these wavelengths, the slight shift in wavelength provides an accurate reference measurement.

The etalon based technique of the present invention provides several advantages over broad band measurement and reference windows. First, the correlation wavelengths are more specifically tailored to correlate with the absorption lines of the gas. The correlation may be further improved with the use of a reflective Fabry-Perot etalon, as will be described. The reflective Fabry-Perot etalon provides increased finesse for the correlation and anti-correlation wavelengths. By increasing the finesse of the wavelengths, nearly all of the correlation radiation may be absorbed by the gas while very little of the anti-correlation radiation is absorbed. The presence of a gas therefore produces an improved change in the relative intensities of the signals reaching the optical sensor during correlation and anti-correlation measurements. This increases the accuracy and selectivity of the detector. Also, to decrease interference and false signals, the narrower correlation and anti-correlation wavelengths may more easily avoid the absorption lines of other gases.

Second, the wavelength change between the correlation and anti-correlation measurements is very small. Accordingly, transmission strength should not vary significantly between the correlation and anti-correlation wavelengths when a gas is not present.

Third, the etalon of the present invention may be modulated at a sufficiently high frequency to detect trace amounts of gas when a survey vehicle is driven at higher speeds.

The preceding provides a general overview of spectroscopic technology and the etalon technique of the present invention. However, a specific detection strategy is employed to detect natural gas leaks.

Natural gas is comprised primarily of methane and ethane. Therefore, to detect natural gas, the detection strategy must target either methane or ethane. Because natural gas is comprised of approximately 90% methane, methane is the leading candidate for detection.

However, methane suffers from certain disadvantages. Methane is a naturally occurring gas with a typical atmospheric concentration of 1.6 ppm. Methane is present in even greater concentrations in certain areas as a result of automobile emissions, swamp gas, and decaying vegetation. Also, atmospheric methane absorbs its characteristic spectrum from sunlight traveling through the atmosphere. If sunlight reaches the optical sensor, the sensor may mistake the methane absorption spectrum in sunlight for methane in the detection beam. Accordingly, targeting methane may lead to false positive readings.

Ethane, in contrast, is not significantly present in the atmosphere. Therefore, the presence of ethane is a more reliable indicator of natural gas. Unfortunately, natural gas is comprised of only approximately 4% ethane. Thus, ethane is much more difficult to detect.

Despite the higher possibility of false positive readings, the relative abundance of methane in natural gas makes methane a more effective detection target. However, the scope of the present invention is not limited to targeting methane. A detection strategy has been devised for both methane and ethane.

Figure 8:
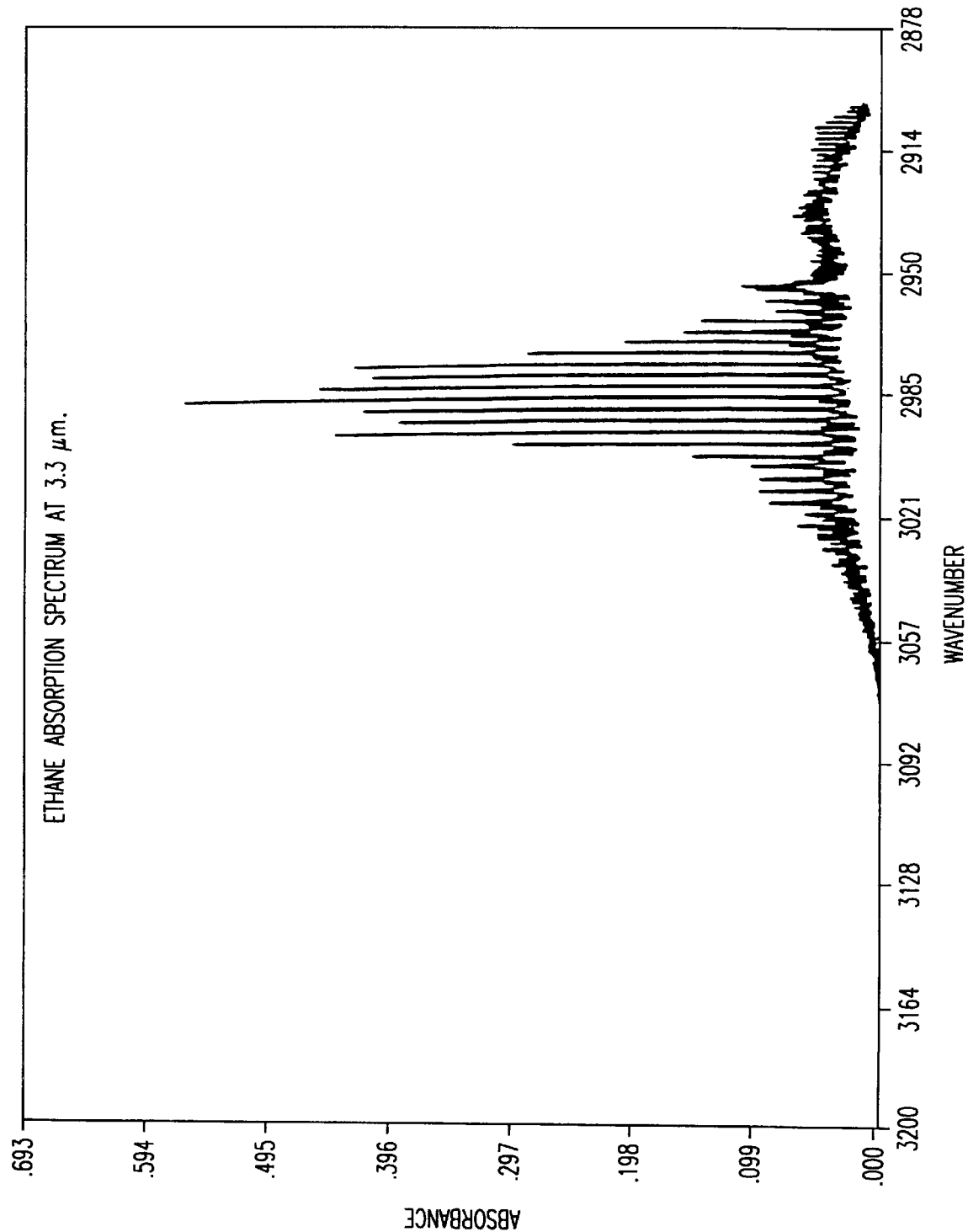
FIG. 8 is a graph of the absorption line spectrum for ethane at 3.3 µm.
Figure 9:
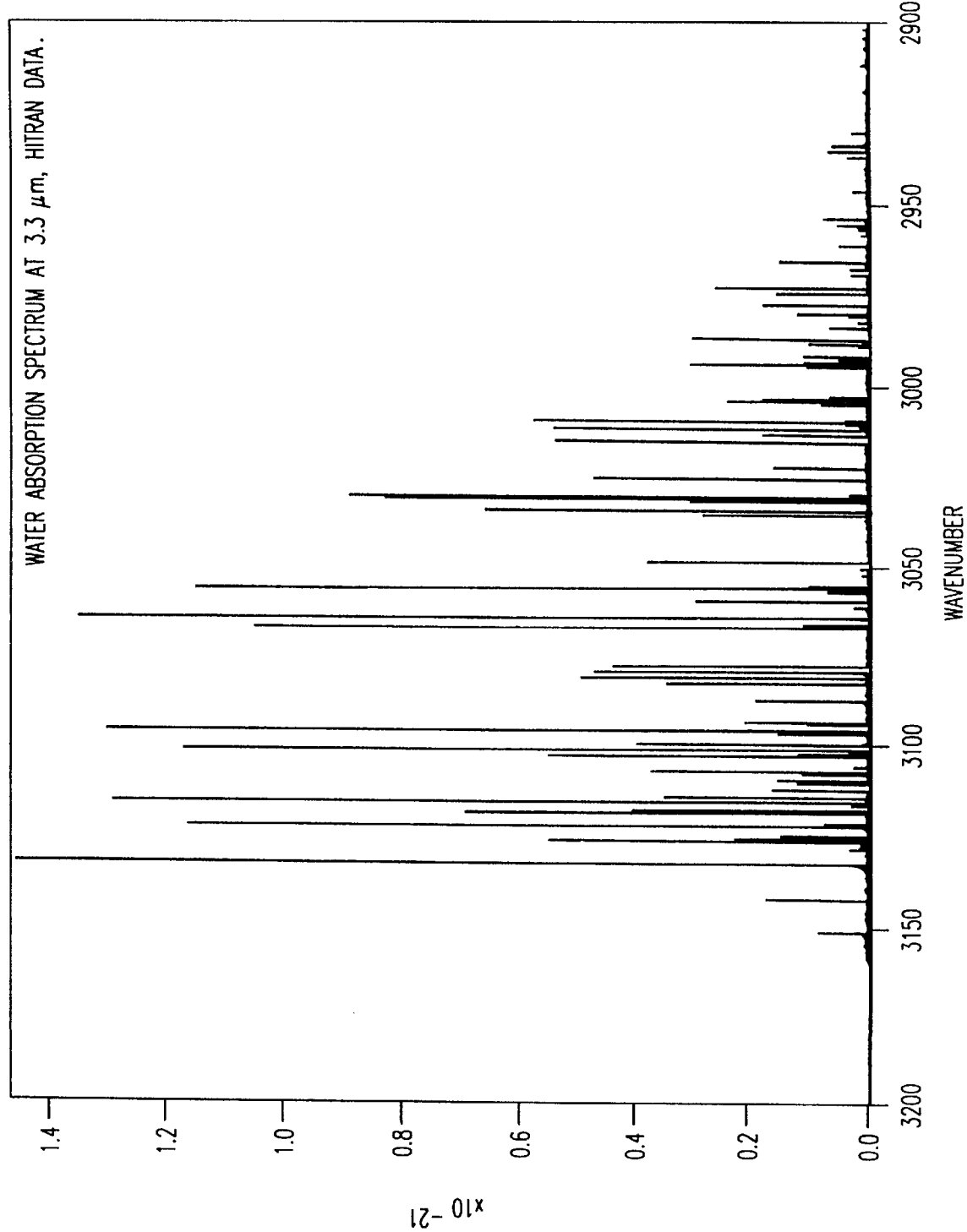
FIG. 9 is a graph of the absorption line spectrum for water at 3.3 µm.

The absorption spectra for methane and ethane at 3.3 μm are shown in FIGS. 5 and 8, respectively. At the wavelength range shown in the graphs, the absorption lines for methane and ethane are relatively regularly spaced. Because the absorption lines are regularly spaced, the lines provide an excellent target for the periodic wavelengths of a measurement transmission. However, as shown in FIG. 9, water vapor also exhibits absorption lines in the 3.3 μm wavelength range.

Water vapor absorption lines present a significant obstacle to the detection of natural gas. Although the absorption lines of water vapor are relatively weak, the abundance of water vapor more than compensates for the weakness. For example, at 20° C. and 100% relative humidity, water vapor's atmospheric concentration is 23,000 ppm. Therefore, to detect ethane or methane at a concentration of 1–2 ppm, the correlation wavelengths should avoid overlapping the water vapor absorption lines. Alternatively, if the correlation wavelengths must overlap water lines, the effect of the water should be relatively equal at the correlation and reference wavelengths. When targeting ethane, the absorption lines produced by atmospheric methane must also be avoided.

To determine the optimum frequencies for detecting a target gas and avoiding water vapor, the precise frequencies of the absorption lines for methane, ethane, and water are needed. To determine overlap, the halfwidths of the absorption lines are also needed. Finally, to evaluate a particular frequency, the absorbance of each gas at that frequency must be known. If frequencies, halfwidths, and absorbencies are Known, the absorption line strengths may be calculated and compared. Also, absorption line strengths are needed to predict signal-to-noise ratios for natural gas leak detection.

Absorption data for methane and water vapor is available from the High-Resolution Transmission Molecular Absorption Database (HITRAN) compiled by the Air Force Geophysics Laboratory. Some absorption data for ethane has been published, for example in C. P. Rinsland et al., 25 Applied Optics 2872 (1986). The necessary data may also be collected with a spectrometer, such as the Nicolet Fourier Transform Spectrometer. After collecting the data, absorption line strength may be calculated.

At a particular frequency, the absorption line strength S is calculated according to the following formula:

$$\Sigma S = -\pi (\Delta v/2) 2.304 \, (A/NL) \quad (1)$$

$\Delta v$ is the halfwidth of the absorption line. A is the absorbance of the absorption line. N is the number of molecules per cubic centimeter in the detection path. L is the length of the detection path. S is typically represented in units of $cm^{-1}$ (molecules $cm^{-2}$).

Using the preceding formula, the absorption line strength at a particular frequency of the target gas, methane for example, may be calculated. Then, the line strengths of any water vapor absorption lines within the width of the methane absorption line may be summed. The ratio of the water absorption line strengths to the methane absorption line strengths indicates the value of that particular frequency as a detection target. If the ratio of water absorption to methane absorption is very low, the presence of methane is more easily detected at the frequency. Further, the absorption line strengths of neighboring or periodic frequencies may be summed to determine the target value of a set of absorption lines.

Although an effective target spectrum may be calculated according to the preceding method, the etalon design should also be considered when evaluating the optimum frequencies for detecting a target gas. The etalon has certain capabilities and characteristics that affect the selection of the optimum frequencies.

The general concepts of birefringent etalon design are well known. A birefringent material, such as crystalline quartz or lithium niobate, has different indices of refraction along its vertical and horizontal axes. If polarized light enters the birefringent material at a 45° angle to the axes, two orthogonal components of equal amplitude are produced. Traveling through the birefringent material, one component is delayed relative to the other. If the components are recombined by a second polarizer after exiting the birefringent material, the components interfere with each other and produce a light wave of periodic wavelengths.

Figure 10:
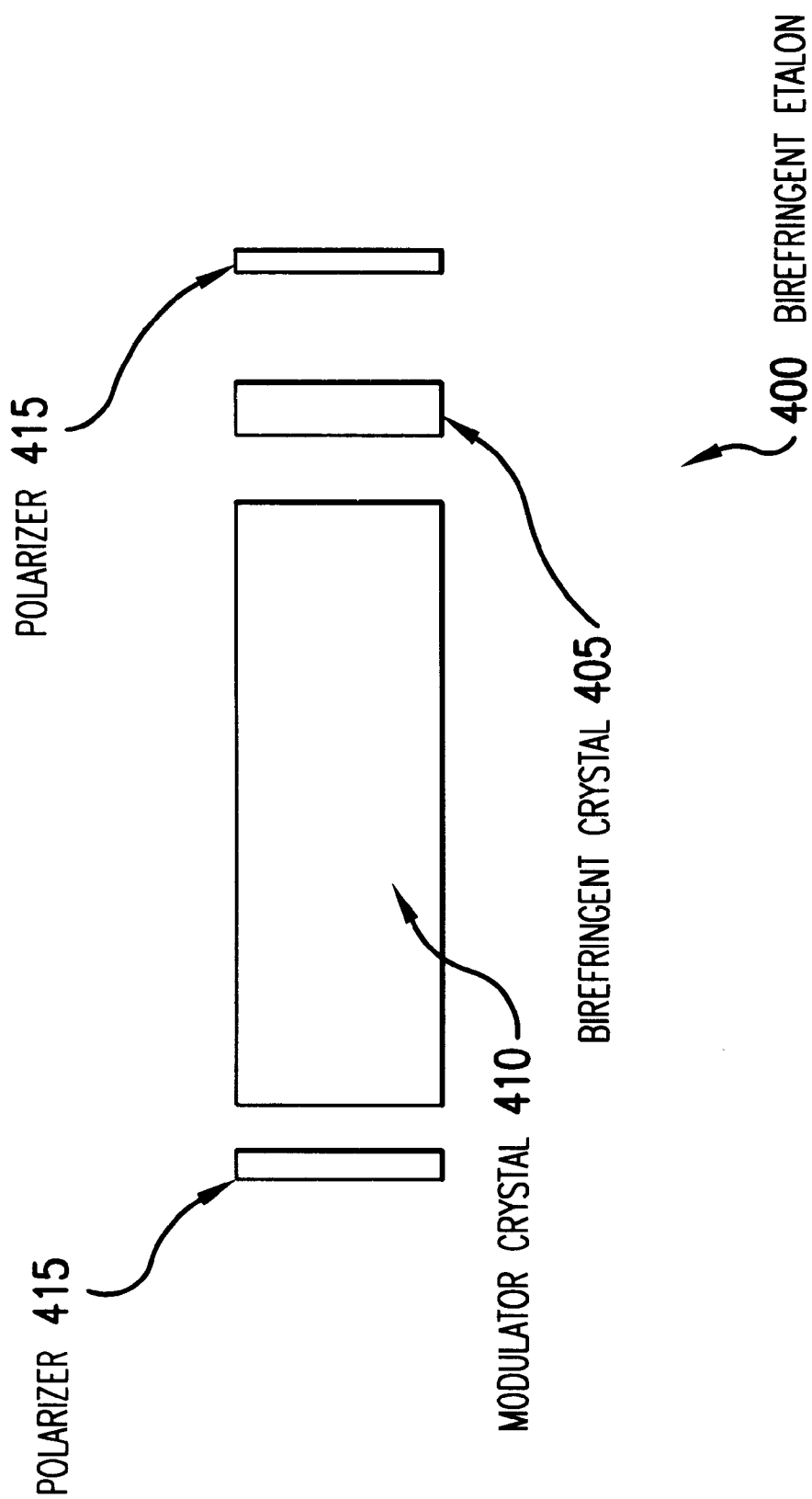
FIG. 10 is a schematic diagram of the basic components of a birefringent etalon.

The basic components of a birefringent etalon 400 are shown in FIG. 10.

A birefringent crystal 405 may be constructed so that it creates periodic wavelengths of light that match the absorption lines of a gas to be detected. For a given material, the length of the birefringent etalon 400 determines the transmission spectrum of the etalon. The periodic wavelengths of light may be shifted by a modulator crystal 410, as shown in the diagram, to produce an anti-correlation or reference signal. The wavelengths may be shifted by several well known modulation means including electro-optical, piezoelectric, or acousto-optical modulators. The wavelengths may also be modulated by mechanical means. However, mechanical modulators, such as filter wheels or movable mirrors, do not offer the speed and precision of other modulation means.

Polarizers 415 may also be provided.

The birefringent etalon 400 shown in FIG. 10 has a transmission T calculated according to the following formula:

$$T = \sin^2 \, (\pi (n_o - n_e) \, Ln) \quad (2)$$

L is the thickness of the etalon. $(n_o - n_e)$ is the birefringence of the etalon, the difference between the ordinary and extraordinary indices of refraction. Frequency of the light, n, is measured in wavenumbers ($cm^{-1}$).

As shown in FIG. 7b, the transmission of the etalon varies periodically between 100% and 0% as a function of the frequency. The spacing between the transmission peaks, referred to as the free spectral range, is calculated according to the following formula:

$$\Delta v = 1/((n_o - n_e) \, L) \quad (3)$$

The free spectral range $\Delta v$ is inversely proportional to the product of the thickness L of the etalon and the birefringence of the etalon $(n_o - n_e)$.

For methane in a certain wavelength range, the absorption line spacing is approximately 9.3 $cm^{-1}$. By choosing the thickness of the birefringent material L, and orienting the crystal axis to determine birefringence $(n_o - n_e)$, the transmission spacing may be matched to the spacing of methane's absorption lines. By selecting the proper frequency of light, the properly spaced transmission bands will fall on the methane absorption lines. When modulated, the transmission spectrum of the etalon switches to a longer wavelength and off the absorption lines. There, the reference measurement may be made. For an electro-optical modulator, the shift in wavelength is determined by adjusting the voltage applied to the modulator.

Although the birefringent etalon 400 may be used to detect ethane and methane, the birefringent etalon 400 transmits relatively broad light bands. Broad bands are not sufficiently discriminating at wavelengths with severe interference from other gases. However, the performance of the system may be improved by using a reflective, or Fabry-Perot, etalon 430.

Figure 11:
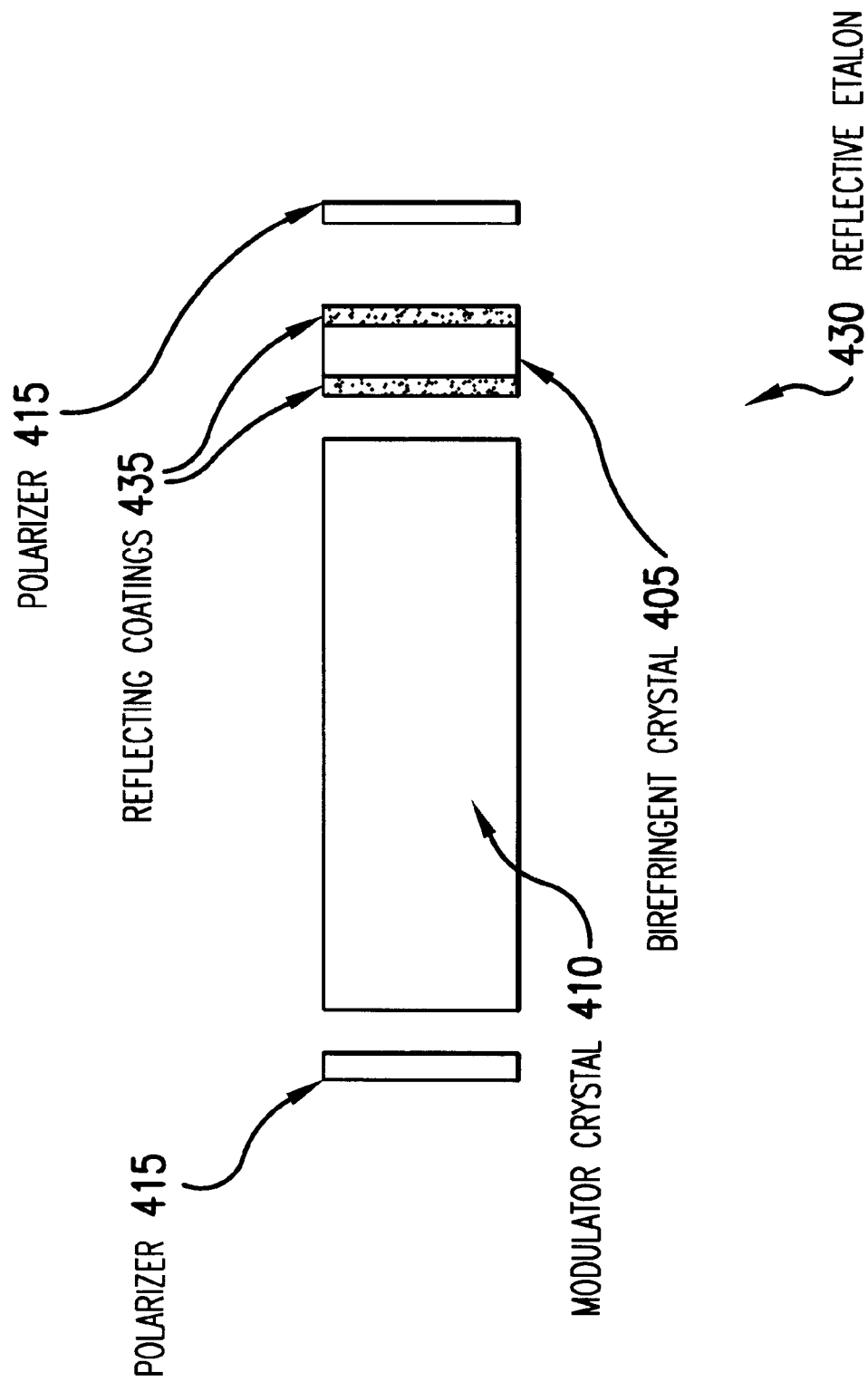
FIG. 11 is a schematic diagram of the basic components of a reflective etalon.

The reflective etalon 430 is shown in FIG. 11 wherein like numerals represent like parts. The birefringent crystal may be given reflecting coatings 435. The coatings 435 act as mirrors and cause multiple reflections within the etalon. The multiple reflections create a much more selective and precise transmission.

Although the crystal may be birefringent, it need not be. A reflective etalon may be created from the mirrored surfaces alone. In that event, the transmission T of the etalon is simply a function of the distance L between the mirrored surfaces. The selectivity of the reflective etalon's transmission T is determined by the reflectivity R of the coating, according to the following formula:

$$T=(1-R)^2/( (1-R)^2+4 R \sin^2 (2\pi N1\ v) )  \quad (4)$$

Figure 12:
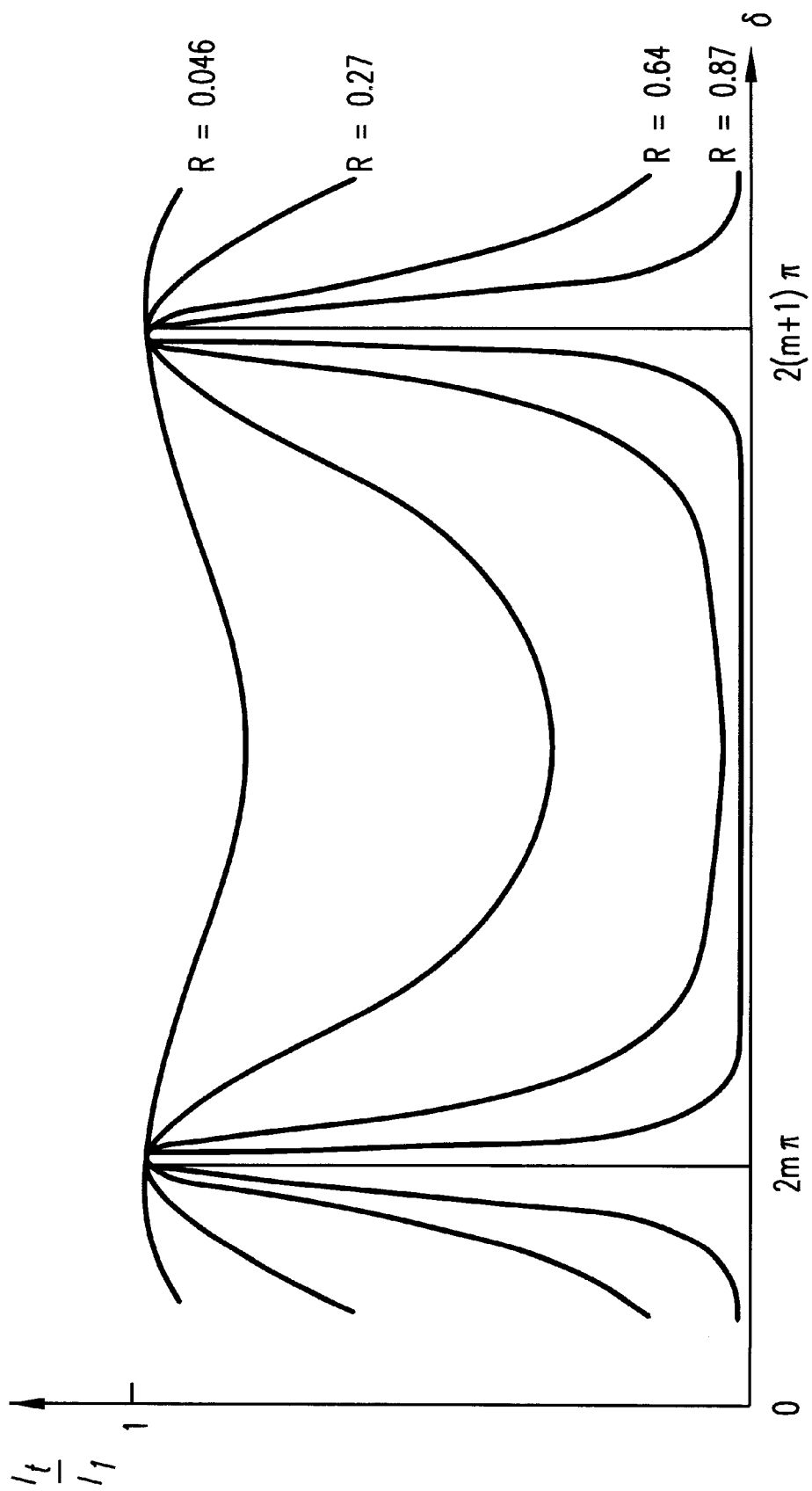
FIG. 12 is a graph of the transmission of a reflective etalon.

FIG. 12 graphically represents the increased selectivity of the transmission as a function of the reflectivity of the coatings. As reflectivity is increased, the reflective etalon transmits narrower bands. At low reflectivity, such as at R=0.27, the etalon transmits broad bands with significant transmission occurring between the peaks. At high reflectivity, such as at R=0.87, the etalon transmits very narrow bands with little or no transmission occurring between the peaks.

Despite the selectivity advantages of narrow transmission bands, the bands may not be too narrow. The bands should be wider than the absorption lines of the target gas. In the case of methane, the transmission bands should be wider than 0.12 cm$^{-1}$. Also, the absorption lines are not perfectly periodic. The spacing between absorption lines increases slightly at increasing wavelengths. As more lines are included in the periodic transmission bands, the increased spacing between absorption lines becomes a factor. Therefore, the transmission bands must be wider so that all absorption lines fall within the transmission bands. Finally, a high reflectivity causes transmission loss. Considering these factors, etalons with a reflectivity of 65–85% generally provide the best overall performance.

Although shown as separate components in FIG. 11, the modulator and etalon may be combined into a single component. In the preferred embodiment, a lithium niobate modulating etalon is used.

As shown by the preceding discussion, many factors must be considered when designing an etalon for detecting a specific gas. The proper portion of the spectrum must be targeted. Methane, for example, exhibits strong and regularly shaped absorption lines in the R-branch of its absorption spectrum at 3150 to 3029 cm$^{-1}$ range. However, in this range, water absorption lines are abundant. In contrast, methane absorption lines in the P-branch, from 2999 to 2907 cm$^{-1}$ range are less defined, but are also less affected by water. Also, the number of absorption lines to measure and the selectivity of the transmission bands must be selected. If few lines are targeted, the reflective etalon may be very selective and utilize narrow transmission bands. However, as a result, the transmission signal may be unacceptably weak.

These factors may be analyzed with a spreadsheet database and program. Using the absorption spectrum data previously described, the frequencies and line strengths for selected methane, ethane, and water absorption lines were entered in the database. To determine an embodiment of the optimum etalon design, 190 methane absorption lines from 3200 to 2870 cm$^{-1}$, 645 water absorption lines in the same range, and 125 ethane absorption lines from 3004 to 2964 cm$^{-1}$ are entered in the database. This data is then used to select an optimum set of target absorption lines and, correspondingly, the design of the etalon. The data may also be used to calculate an overall absorption value for use in signal-to-noise calculations.

A representative portion of the database for methane is reproduced in FIG. 14. The frequencies and line strengths of the methane absorption lines are listed in columns A and B, respectively, beginning at line 152. With this data, potential etalon design parameters may be tested.

Input parameters are entered in column C, beginning at line 2. Etalon reflectivity is entered in cell C2. The free spectral range of methane absorption lines in the wavelength range to be tested is entered in cell C3. The amount of gas in the detection path, expressed in ppm times the pathlength, is entered in cell C4. The center absorption line at the target wavelength is entered in cell C6. The upper and lower absorption line targets are entered in cells C7 and C8.

If the range of absorption line targets is large, a stronger signal will reach the optical detector. However, to maintain overlap of the etalon transmission lines on the absorption lines, the transmission lines must be broader. This may result in increased interference from water. A smaller range permits higher selectivity and produces better sensitivity, but results in a lower signal strength.

The modulation percent is entered in cell C9. The modulation percent defines where the reference measurements are made. At 50% modulation, the reference measurements are made midway between the transmission peaks.

From these input parameters, the program calculates the dimensions of the etalon in cell H2. The product of the refractive index n and the thickness L of the etalon is 0.049 cm. The resolution of the etalon (the width of the transmission bands) is calculated in cell 113. The resolution exceeds the 0.12 cm$^{-1}$ width of a methane absorption line, as required. The total number of molecules of methane in the detection path is calculated in cell H4.

The amount of light absorbed by the gas is calculated in the lower portion of the spreadsheet. Assuming a flux of light incident on the etalon of 1 unit per wavenumber, the flux incident on the etalon is the difference between the upper and lower frequency limits. This value is calculated in cell G10. The amount of light transmitted by the etalon, in this case 14.12 cm$^{-1}$ or about 18% of the light incident on the etalon, is calculated in cell G11.

From these figures, the spreadsheet program calculates the transmission characteristics for each of the absorption lines of methane within the range considered. The frequency and line strength of each absorption line is listed in columns A and B. Columns C and E show the calculated etalon transmission at each frequency for the measurement (on line) and reference (off line) signal. In columns G and H, the etalon transmission is multiplied by the line strength (from column B) and the number of molecules in the detection path (from cell H4) to calculate the absorption of the signal. The measurement signal is calculated in column G and the reference signal is calculated in column H.

The total measurement signal absorption is summed in cell G15. The total reference signal absorption is summed in cell H15. Ideally, the measurement signal absorption is large and the reference signal absorption is small. To compare the chosen parameters with other sets of input parameters, the ratio of on line absorption to off line absorption is computed in cell G12. The optimum etalon design maximizes this ratio.

The absorption lines for water may be entered and calculated in a similar program. The absorption of both water and the target gas may then be compared at a specific set of frequencies. Ideally, water causes little or no absorption at the measurement and reference frequencies. However, water absorption lines are present throughout the spectrum and difficult to avoid. Therefore, the optimum set of parameters equalizes the water absorption at the measurement and reference frequencies.

The spreadsheet shown in FIG. 15 calculates absorption data for both methane and water. For ethane, as shown in FIG. 16, the spreadsheet must calculate absorption data for ethane, water, and methane.

The input parameters may be varied to determine the optimum etalon design. In an embodiment, the etalon is preferably a LiNb modulating etalon. The spreadsheet program offers the benefit of performing multiple "what if" calculations. For example, the reflectivity of the etalon may be raised or lowered to determine its effect on the absorption ratio. Similarly, the target frequencies may be changed and the absorption results seen immediately.

FIG. 15 discloses one set of parameters for detecting natural gas. These parameters detect methane in the 3.3 $\mu$m wavelength range. The spectral band used in this design extends from 3069 to 3110 cm$^{-1}$ and includes five of the strongest lines in the R-branch of the methane absorption band. At this range, as shown in cell G17, the measurement signal absorption for methane is nearly 75 times higher than the reference signal absorption. Although the water absorption at 20° C. and 100% humidity is 10 times higher than methane absorption, this particular etalon design closely equalizes the water absorption for the measurement and reference signals.

However, a preferred set of parameters for detecting methane is shown FIG. 17. This etalon design targets methane absorption lines in the P-branch of the methane spectrum. As is shown in FIG. 17, the absorption caused by water is nearly identical at the measurement and reference frequencies. Therefore, the water absorption lines do not significantly affect the contrast of the methane signal.

An etalon for detecting ethane may also be designed according to the method described above. However, as previously discussed, the ethane etalon must discriminate from both water and methane. In addition, the ethane absorption lines intersect or closely correlate with water and/or methane at many points. This problem was overcome by doubling the free spectral range of the ethane etalon.

Figure 13:
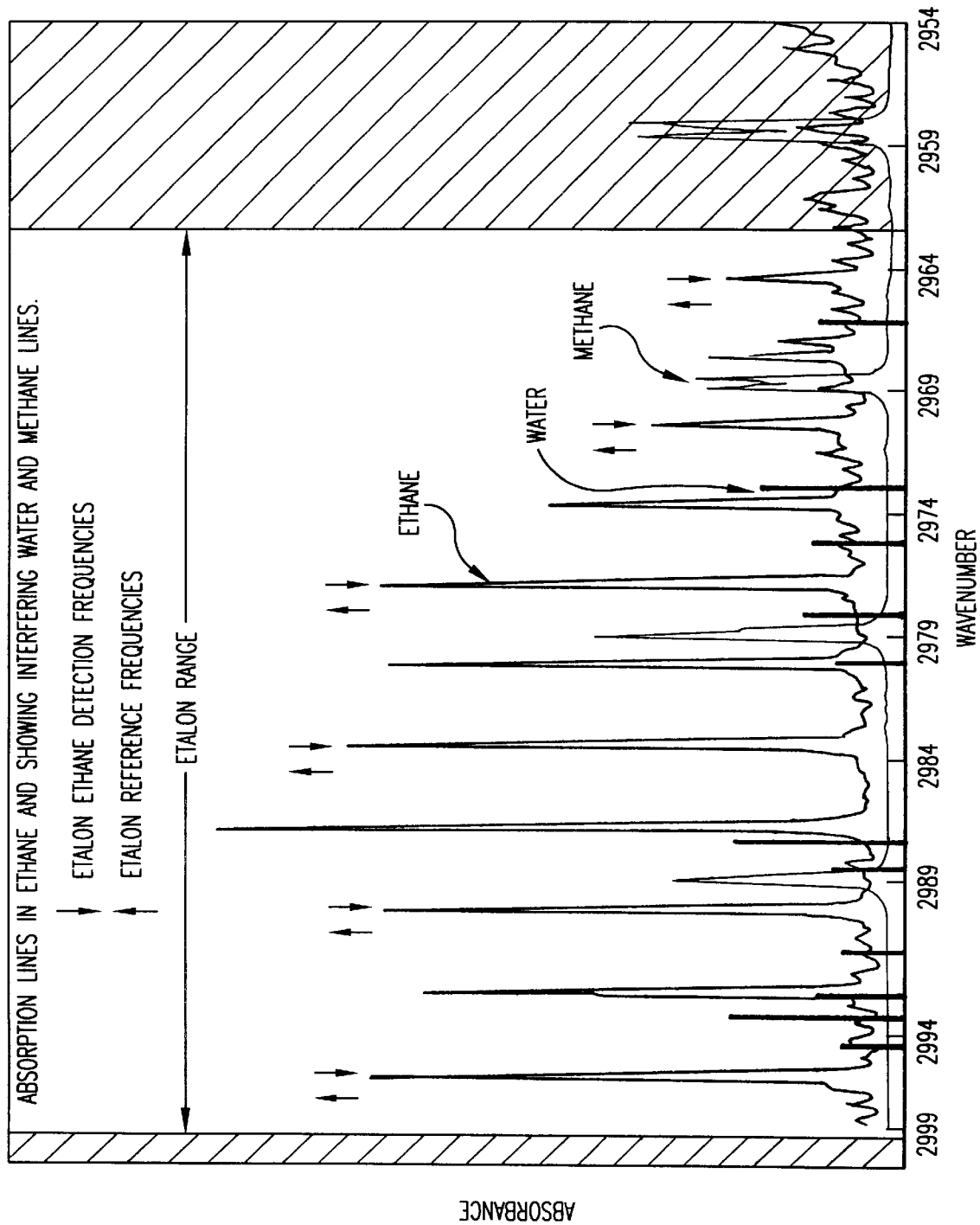
FIG. 13 is a graph of the absorption lines for ethane, methane, and water at a selected portion of the spectrum.

The overlapping spectra of ethane, methane, and water is shown in FIG. 13. As can be seen, the absorption lines for ethane intersect or closely correlate with water and methane lines at several points. However, by correlating the etalon transmission with alternating ethane absorption lines at the range shown, the interference was greatly diminished.

With the free spectral range of the etalon doubled, the etalon directs correlation transmission bands only to every other ethane absorption line. The ethane absorption lines that are in proximity to water and/or methane lines are avoided. Although half the available line strengths were sacrificed, this innovation considerably improved the detection capabilities of the etalon. In FIG. 13, the measurement transmissions are represented by downward pointing arrows and the reference transmissions are represented by the upward pointing arrows.

The 1.6 $\mu$m spectrum was also considered as a potential range for detection. However, the 3.3 $\mu$m spectrum was ultimately selected as a detection target. The 1.6 $\mu$m spectrum initially appeared to offer the advantages of a greater signal-to-noise ratio and less expensive detection equipment. Also, the 1.6 $\mu$m band is close to the 1.5 $\mu$m band traditionally used for fiber optic applications. Fiber optics offered the alternative of directing the transmission beam to detection devices located inside the survey vehicle.

However, 1.6 $\mu$m detection equipment proved less reliable than 3.3 $\mu$m band equipment. Therefore, the 3.3 $\mu$m band has proven to be the preferred wavelength band for detection. The inventors anticipate, however, that equipment improvements and technological developments will make the 1.6 $\mu$m wavelength band a viable location for practicing the device and method of the present invention. Therefore, the present invention is not limited to the 3.3 $\mu$m wavelength band.

Compared to its absorption spectrum at 3.3 $\mu$m, the absorption spectrum for ethane at 1.6 $\mu$m is weak. Also, the irregular absorption lines of the ethane spectrum at 1.6 $\mu$m are much less suitable for detection with an etalon. In contrast, the methane absorption spectrum at 1.6 $\mu$m is relatively periodic with a line spacing of 9.83 wavenumbers. The parameters for detecting methane at 1.6 $\mu$m are disclosed in Table 5.

As shown in cell G15 of FIG. 18, the summed absorption of the methane lines in the 1.6 $\mu$m range is relatively weak. The methane line strength is roughly 100 times weaker than in the 3.3 $\mu$m range. However, water interference is also roughly 10 times lower. Also, the weak methane absorption line strength may be compensated to some extent by the better detectors that are available for the 1.6 $\mu$m range. Accordingly, the 1.6 $\mu$m may prove attractive for measuring higher concentrations of methane or for measuring methane over a longer detection path length.

Although a preferred embodiment of the present invention has been disclosed, many alterations and modifications of the preferred embodiment are within the scope of the present invention. For example, a natural gas detection device for use on a survey vehicle has been disclosed. However, a smaller, portable gas detector would also fall within the scope of the present invention. The portable detector could be used to conduct walking surveys of natural gas leaks. A stationary natural gas detector for use in a home, office, or factory could also employ the teachings and fall within the intended claims of the present invention. In addition, a mobile or stationary gas detector with a transmitter and receiver in close proximity to detect a reflected light beam would also practice the inventive aspects of the present invention.

Similarly, the present invention is not limited to either the preferred embodiment or the other embodiments specifically disclosed in this application. For example, an etalon filter with ordered elements has been described. However, the order of the elements in the filter is not crucial to the operation of the etalon filter. The light beam may be filtered and/or modulated prior to directing it through the detection area. Other changes not disclosed in the specification would be obvious to one skilled in the art. Therefore, the scope of the present invention should be determined based on the invention as claimed.

We claim:

1. A method of detecting natural gas comprising the steps of:

providing a vehicle;

mounting a natural gas detector apparatus to the vehicle, the detector apparatus comprising a transmitter section and a receiver section displaced a preselected distance from each other, the transmitter section including a light source;

transmitting a light beam in a beam path from the transmitter section to the receiver section;

driving the vehicle over an area of interest so that natural gas intercepts the beam path and absorbs representative wavelengths of the light beam;

receiving a portion of the light beam in the receiver section so that the light beam is directed into an etalon; and detecting a gas leak in the area of interest from the portion light beam using the gas detection apparatus mounted on the vehicle while the vehicle is in motion.

2. The method of claim 1, further comprising the step of plotting a concentration of the gas leak over time.

3. The method of claim 1, further comprising the step of plotting a concentration of the gas leak over distance.

4. The method of claim 1, further comprising the step of measuring gas concentrations at sampling rates sufficient to allow the vehicle to travel at speeds of at least 10 miles per hour without sacrificing sensitivity.

5. The method of claim 1, further comprising the step of tuning the etalon to transmit at preselected wavelengths corresponding to a preselected set of absorption lines of the gas to be detected.

6. The method of claim 1 wherein the step of driving the vehicle over an area of interest is performed at a speed of not less than 10 miles per hour and not greater than 20 miles per hour.

7. The method of claim 1, further comprising the step of providing response to the presence of a natural gas leak as the vehicle travels over the area of interest with an integration time of less than about 0.1 seconds.

8. The method of claim 1 wherein the step of driving the vehicle over an area of interest is performed at a speed greater than 20 miles per hour.

9. A natural gas detection system comprising:

a vehicle having an odometer; and a natural gas detector apparatus mounted to the vehicle, the detector apparatus including a transmitter section and a receiver section displaced a preselected distance from each other, the transmitter section including a light source transmitting a light beam from the transmitter section to the receiver section forming an exposed beam path therebetween, such that natural gas intercepts the exposed beam path and absorbs representative wavelengths of the light beam, the receiver section receiving a portion of the light beam onto an electro-optical etalon; and a controller constructed and arranged to receive information from the vehicle odometer and from the natural gas detector to facilitate the graphing of gas concentration over the distance traveled by the vehicle.

10. The gas detector system of claim 9 wherein the transmitter section comprises a light source and a reflecting mirror arranged such that the light source impinges upon the reflecting mirror to transmit the light beam through an aperture in the transmitter section forming the beam path between the transmitter section and the receiver section.

11. The gas detector system of claim 9 wherein the receiver section comprises an aperture for receiving a portion of the light beam transmitted from the transmitter section through a lens onto a reflecting mirror to direct the portion of the light beam from the beam path to the electro-optical etalon.

12. A system of claim 9 wherein the etalon is a LiNb modulating etalon tuned to transmit at specific wavelengths corresponding to a specific set of absorption lines of the gas to be detected.

* * * * *